(12) United States Patent
Auguste et al.

(10) Patent No.: US 8,654,074 B1
(45) Date of Patent: Feb. 18, 2014

(54) REMOTE CONTROL SYSTEMS AND METHODS FOR PROVIDING PAGE COMMANDS TO DIGITAL ELECTRONIC DISPLAY DEVICES

(75) Inventors: Donna Marie Auguste, Denver, CO (US); David Edward Hayes, Denver, CO (US)

(73) Assignee: Alpha and Omega, Inc., Denver, CO (US)

( * ) Notice: Subject to any disclaimer, the term of this patent is extended or adjusted under 35 U.S.C. 154(b) by 167 days.

(21) Appl. No.: 13/159,205

(22) Filed: Jun. 13, 2011

Related U.S. Application Data

(63) Continuation-in-part of application No. 12/830,274, filed on Jul. 2, 2010.

(51) Int. Cl.
 *G09G 5/00* (2006.01)
(52) U.S. Cl.
 USPC .......................................................... 345/156
(58) Field of Classification Search
 USPC ......... 345/156, 157, 169, 173, 179, 184, 901, 345/98; 434/98, 161, 176, 307 R, 308, 91; 715/776; 348/375, 734
 See application file for complete search history.

(56) References Cited

U.S. PATENT DOCUMENTS

| | | | |
|---|---|---|---|
| 5,624,265 A * | 4/1997 | Redford et al. ............ 434/307 R |
| 6,229,526 B1 * | 5/2001 | Berstis ........................... 345/158 |
| 6,514,143 B1 * | 2/2003 | Tanaka et al. .................... 463/37 |
| 6,712,701 B1 | 3/2004 | Boylan, III et al. |
| 6,822,635 B2 | 11/2004 | Shahoian et al. |
| 7,379,078 B1 * | 5/2008 | Gossweiler et al. .......... 345/660 |
| 7,386,804 B2 | 6/2008 | Ho et al. |
| 7,587,534 B2 * | 9/2009 | Liu et al. .......................... 710/62 |
| 7,605,873 B2 * | 10/2009 | Tseng et al. ................... 348/729 |
| 7,890,816 B2 * | 2/2011 | Martch et al. ................... 714/57 |
| 7,992,163 B1 * | 8/2011 | Jerding et al. .................. 725/28 |
| 8,157,651 B2 * | 4/2012 | Ohta et al. ....................... 463/37 |
| 8,314,887 B2 * | 11/2012 | Wakisaka ...................... 348/563 |
| 8,436,803 B2 * | 5/2013 | Inoue ............................. 345/102 |
| 2002/0058240 A1 * | 5/2002 | Redford et al. ........... 434/307 R |
| 2003/0214601 A1 | 11/2003 | Yuen |
| 2004/0001085 A1 * | 1/2004 | Iwasaki .......................... 345/738 |
| 2004/0090424 A1 * | 5/2004 | Hurley et al. ................. 345/169 |
| 2005/0147953 A1 * | 7/2005 | Ho ................................. 434/317 |
| 2005/0160468 A1 * | 7/2005 | Rodriguez et al. ............ 725/109 |
| 2005/0260551 A1 * | 11/2005 | Rubin et al. ................... 434/317 |
| 2005/0264702 A1 * | 12/2005 | Yoshii ............................ 348/687 |
| 2006/0097987 A1 * | 5/2006 | Hughes ......................... 345/156 |
| 2006/0109138 A1 * | 5/2006 | Chiang .................... 340/825.69 |
| 2006/0291149 A1 * | 12/2006 | Suzuki et al. ................. 361/679 |

(Continued)

OTHER PUBLICATIONS

Web pages date Mar. 7, 2011 from the website at http://www.airturn.com.

(Continued)

*Primary Examiner* — Joe H Cheng
(74) *Attorney, Agent, or Firm* — TIPS Group

(57) ABSTRACT

A remote control system, set forth by way of example and not limitation, includes a remote control device including one or more controls operative to develop at button control signals in response to activation by a user. An interface device is responsive to the button control signals and is operative to provide device control signals via a wired connection to an electronic display device. The device control signals are operative to control an application running on an electronic display device.

19 Claims, 19 Drawing Sheets

(56) References Cited

U.S. PATENT DOCUMENTS

| | | | |
|---|---|---|---|
| 2007/0079245 A1* | 4/2007 | Oh | 715/740 |
| 2007/0176894 A1* | 8/2007 | Abe | 345/156 |
| 2008/0032276 A1* | 2/2008 | Zheng | 434/317 |
| 2008/0079604 A1* | 4/2008 | Madonna et al. | 340/825.72 |
| 2008/0129692 A1* | 6/2008 | Sween et al. | 345/157 |
| 2008/0145828 A1* | 6/2008 | Yu | 434/308 |
| 2008/0174546 A1* | 7/2008 | Schneider | 345/156 |
| 2009/0073102 A1* | 3/2009 | Herz et al. | 345/98 |
| 2009/0284472 A1* | 11/2009 | Mehta et al. | 345/169 |
| 2010/0023599 A1* | 1/2010 | Azuma et al. | 709/217 |
| 2010/0194715 A1* | 8/2010 | Hurley et al. | 345/179 |
| 2010/0231511 A1* | 9/2010 | Henty et al. | 345/157 |
| 2010/0302190 A1* | 12/2010 | Yeh | 345/173 |
| 2010/0315333 A1* | 12/2010 | Hsu | 345/157 |
| 2011/0109751 A1* | 5/2011 | Chang et al. | 348/207.1 |
| 2011/0111382 A1* | 5/2011 | Binyamin | 434/317 |
| 2011/0248912 A1* | 10/2011 | Chen | 345/156 |
| 2012/0140124 A1* | 6/2012 | Moroney et al. | 348/734 |
| 2012/0274547 A1* | 11/2012 | Raeber et al. | 345/156 |

OTHER PUBLICATIONS

Web pages date Jul. 15, 2011 from the website at http://www.orin.com/access/pagebot/.

* cited by examiner

REMOTE CONTROL SYSTEMS AND METHODS FOR PROVIDING PAGE COMMANDS TO DIGITAL ELECTRONIC DISPLAY DEVICES

CROSS-REFERENCE TO RELATED APPLICATIONS

This application is a continuation-in-part of co-pending U.S. patent application Ser. No. 12/830,274, filed Jul. 2, 2010, entitled, "Remote Control Systems and Methods for Activating Buttons of Digital Electronic Display Devices," and which is incorporated herein by reference in its entirety.

BACKGROUND

Computerization and the advent of flat panel displays have resulted in a proliferation of digital electronic display devices ranging from plasma televisions to cellular telephones. One particularly fast growing segment of the digital electronic display market are devices designed to display e-books, i.e. books that are distributed in electronic form. "E-books" also include, by way of non-limiting examples, non-traditional "books" comprising documents and collections of printable pages such as handwritten documents, notated music (e.g. sheet music), chord charts, "fake music", lead sheets, court documents, dissertations, theses, journals, periodicals, magazine, lab notebooks, and photographs, to name a few.

E-books are usually read on dedicated digital electronic display devices commonly known as e-book readers, although they are increasingly being read on other types of electronic display devices such as computer displays, laptop computers, tablet computers, personal digital assistants (PDAs) and cellular telephones.

Dedicated e-book readers are often based upon electronic paper displays. Electronic Paper (also known as "e-paper" or "electronic ink") is a display technology designed to mimic the appearance of ordinary ink on paper. Unlike a conventional flat panel computer display, which uses a backlight to illuminate its pixels, electronic paper reflects light like ordinary paper. Furthermore, electronic paper is sometimes capable of displaying text and images indefinitely without drawing electricity.

Examples of e-book readers include the Amazon Kindle®, the Sony PRS-700™ and the Barnes & Noble Nook™. Some e-book readers, such as the Amazon Kindle, use mechanical buttons to navigate to and through an e-book, which other e-book readers, such as the Sony PRS-700, use touch-screen display technology. The Barnes & Noble Nook is a hybrid device including an electronic paper screen, mechanical buttons and a small, color touch screen display.

It should be noted that references to the Amazon Kindle refer to a dedicated hardware e-book reader marketed by Amazon, Inc. Amazon also provides Amazon Kindle software which runs on a variety of platforms, such as computers, cell phones and tablet computers, which will be referred to herein as "Kindle Application Programs."

The introduction of the iPad® tablet computer by Apple, Inc. has generated new interest and has heightened competition in the e-book market. The iPad has a full-color touch-screen display and therefore has the benefits and disadvantages of backlit, flat panel computer displays. The iPad uses its touch-screen for e-book navigation. The iPad is provided with e-book reader software, and can also, for example, run Kindle Application Programs for the purpose of buying and reading e-books sold and/or delivered wirelessly by Amazon.

E-book readers are generally intended to be handheld devices and are controlled by pressing a button, either mechanical or virtual, or by making gestures with a finger on a touch screen display. However, there are times when it would be desirable to be able to control a digital electronic display device, such as an e-book reader, without actually touching the device. For example, a musician might desire to use an e-book reader to display sheet music and would not have a hand free for "turning" the pages of the e-book. As another example, a person engaging in a physical activity, such as running on a treadmill, may wish use an e-book reader that is propped up and out of convenient reach. Furthermore, handicapped persons may be physically incapable of using their hands to hold and/or control an e-book reader.

With respect to the last example set forth above, there have been devices made for the handicapped to aid in the reading of ordinary books. For example, Zygo Industries, Inc. markets a manual page turner for conventional books which allows a handicapped person to use a joystick to turn pages forward and backward, one at a time or continuously (e.g. when scanning a chapter or a directory). However, manual page turners of the prior art are unsuitable for use with e-book readers and other forms of digital electronic display devices.

These and other limitations of the prior art will become apparent to those of skill in the art upon a reading of the following descriptions and a study of the several figures of the drawing.

SUMMARY

A remote control system, set forth by way of example and not limitation, includes a remote control device including one or more controls operative to develop at button control signals in response to activation by a user. An interface device is responsive to the button control signals and is operative to provide device control signals via a wired connection to an electronic display device. The device control signals are operative to control an application running on an electronic display device. In some embodiments the application displays an image, such as a document page, on a display of the electronic display device, and the device control signals are operative to control the display of the image.

In another remote control system, set forth by way of example and not limitation, at least one control is operative to develop at least one activation signal in response to activation by a user. Logic circuitry coupled to the at least one control is operative to receive the at least one activation signal, and includes a wireless transmitter operative to transmit at least one device control signal wirelessly to an electronic display device responsive to the at least one device control signal. The device control signal is operative to control an application running on the electronic display device to change a display of a document displayed by the application on the electronic display device. In some embodiments the change of the display of the document can include displaying a different page of a displayed document in response to the at least one activation signal.

A method for remotely controlling an electronic display device, set forth by way of example and not limitation, includes providing a button control signal from a remote control device in response to a control on the remote control device being activated by a user. The method further includes receiving said button control signal at an interface device, decoding said button control signal using a digital processor to derive a device control signal, and providing the device control signal to an electronic display device, the at least one device control signal operative to control an application running on an electronic display device.

These and other combinations and advantages and other features disclosed herein will become apparent to those of skill in the art upon a reading of the following descriptions and a study of the several figures of the drawing.

BRIEF DESCRIPTION OF THE DRAWINGS

Several examples will now be described with reference to the drawings, wherein like components are provided with like reference numerals. The examples are intended for the purpose of illustration and not limitation. The drawings include the following figures.

DETAILED DESCRIPTIONS

Figure 1:
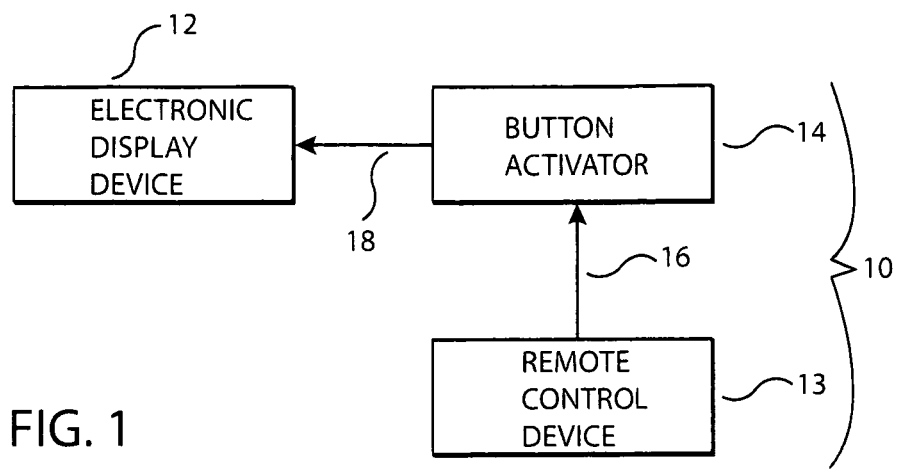
FIG. 1 is a block diagram of an example remote control system for activating buttons of a digital electronic display device.

FIG. 1 is a block diagram of an example remote control system 10 for activating the buttons of a digital electronic display device 12. In this example, the remote control system 10 includes a remote control device 13 and a button activator 14 which can communicate via an interface 16. The button activator 14 can communicate with the digital electronic display device 12 via an interface 18.

As used herein, a "digital electronic display device", "electronic display device", "display device" or the like will refer to any digital electronic device having a screen or display with addressable pixels. Non-limiting examples of digital electronic display devices include e-book readers, desk computers, laptop computers, netbook computers, table computers, personal digital assistants (PDSs) and cellular telephones. The vast majority of current digital electronic display devices use flat-panel displays based upon a variety of technologies including volatile display technologies such as light-emitting diode display (LED), liquid crystal display (LCD) and plasma display technologies and static display technologies such as electronic paper.

Digital electronic display devices typically include a number of buttons to control their functionality. These buttons can be of various technologies, including mechanical buttons, capacitively coupled buttons, touch screen buttons, etc. As used herein, a "button" associated with a digital electronic display device will include any real (e.g. mechanical or capacitive) or virtual (e.g. a button image or the like on a touch screen) button which, when pressed, signals the digital electronic display device to perform some function or act. By "press" or "activated" it is meant that the button, real or virtual, is capable of being engaged by, for example, by a finger or a stylus, although buttons can be pressed or activated in other fashions as well. Furthermore, "press" or "activation"

can also include gesturing, e.g. such as an engagement with a touch screen display and subsequent movement in contact with the screen.

Digital electronic display devices are becoming increasingly small and portable. Often, they are meant to be handheld devices. The buttons on such displays may be mechanical (such as on the Kindle® e-book reader) or virtual on a touch-screen display (such as on the iPad® tablet computer). Still other digital electronic display devices include both real and virtual buttons.

Button activator 14 is often closely associated with digital electronic display device 12. In some cases, button activator 14 is mechanically engaged with digital electronic display device 12, i.e. the interface 18 is mechanical. In other cases, button activator 14 may be a part of the digital electronic display device 12 or be physically separated from the digital electronic display device 12.

Remote control device 13 is generally physically separated from the digital electronic display device 12. In some cases, remote control device 13 is physically separated from button activator 14. In other cases button activator 14 may be a part of the remote control device 13. Remote control device 13 can be used to develop button control signals. By way of example and not limitation, remote control 13 can develop page turn signals for an e-book device such as "Page Forward" and "Page Back" signals.

In the following descriptions, remote control system 10 will be discussed with reference to the specific examples such as the Kindle-DX® e-book reader provided by Amazon, Inc. and the iPad tablet computer provided by Apple, Inc. These examples are not to be seen as limiting but, rather, illustrative of the general concepts set forth herein.

Figure 2:
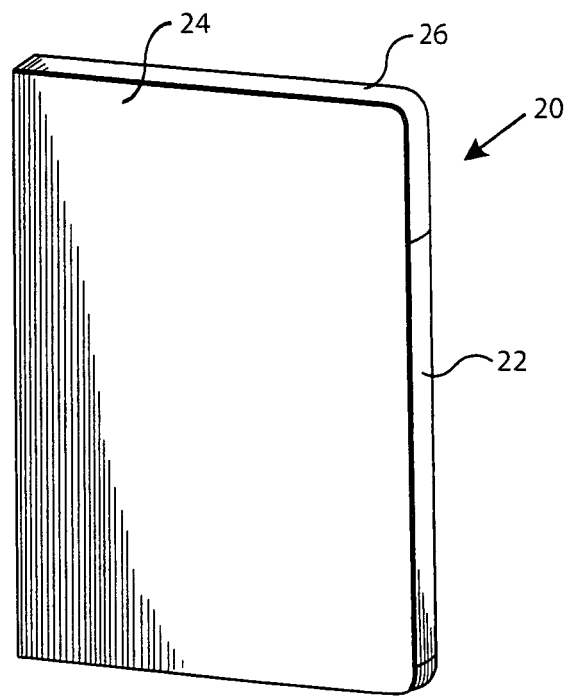
FIG. 2 is a perspective view of an example cover for an e-book reader with an example integrated button activator in a closed configuration.

FIG. 2 is a perspective view of cover 20 for an e-book reader having an integrated button activator 22. The cover is 20 illustrated in its closed position and has a front cover 24 and a back cover 26. The material of cover 20 is preferably thin, yet strong, to protect the e-book reader that may be stored therein. The material, or materials, of at least the back cover 26 are, by way of non-limiting example, sufficiently rigid to provide mechanical stability for the button activator with respect to an e-book reader engaged with, for example, back cover 26.

Figure 3:
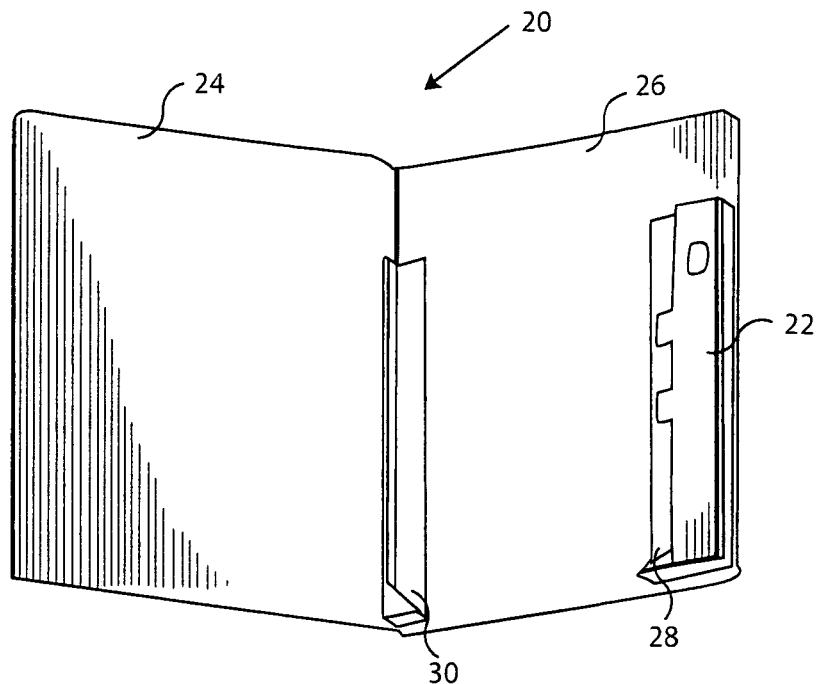
FIG. 3 is a perspective view of the cover of FIG. 2 in a partially opened configuration.

FIG. 3 is a perspective view of the inside of the cover 20 in a partially open configuration. Button activator 22 is attached to the inside of the back cover along its right edge. Part of the button activator 22 includes a frame 28 which is configured to engage the right edge of an e-book reader, such as the Kindle-DX e-book reader. A complementary frame 30 is attached proximate to the left edge of the inside of back cover 26.

Figure 4:
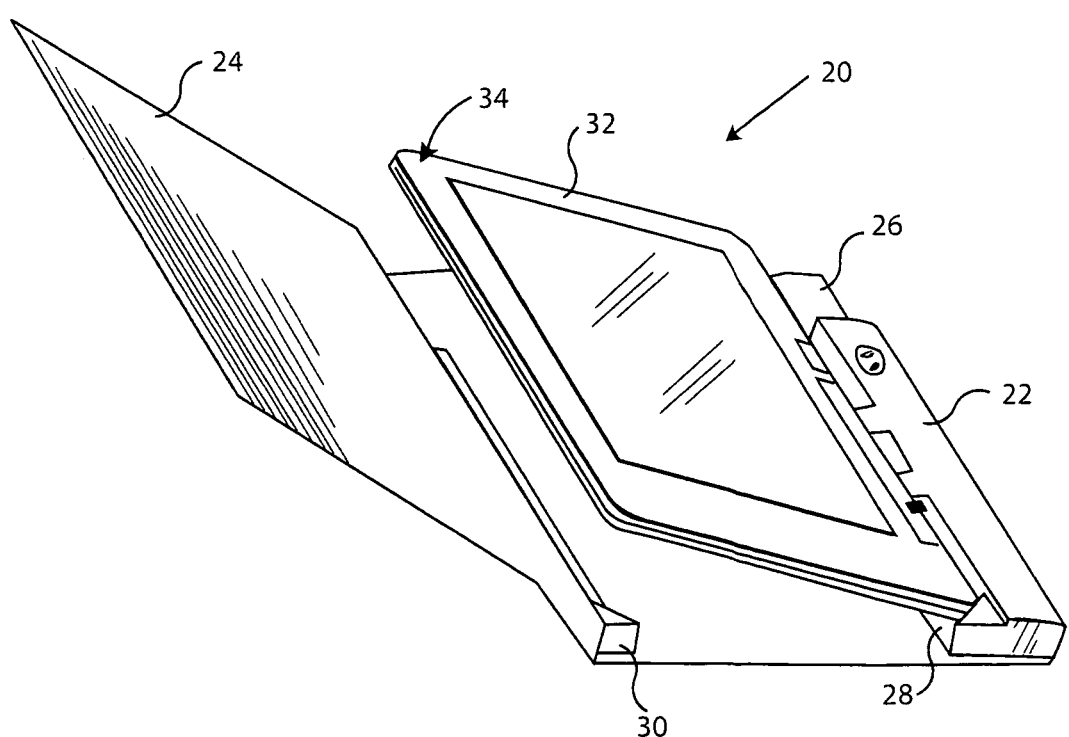
FIG. 4 is a perspective view of the cover of FIG. 3 with an example e-book reader partially engaged with the integrated button activator.
Figure 5:
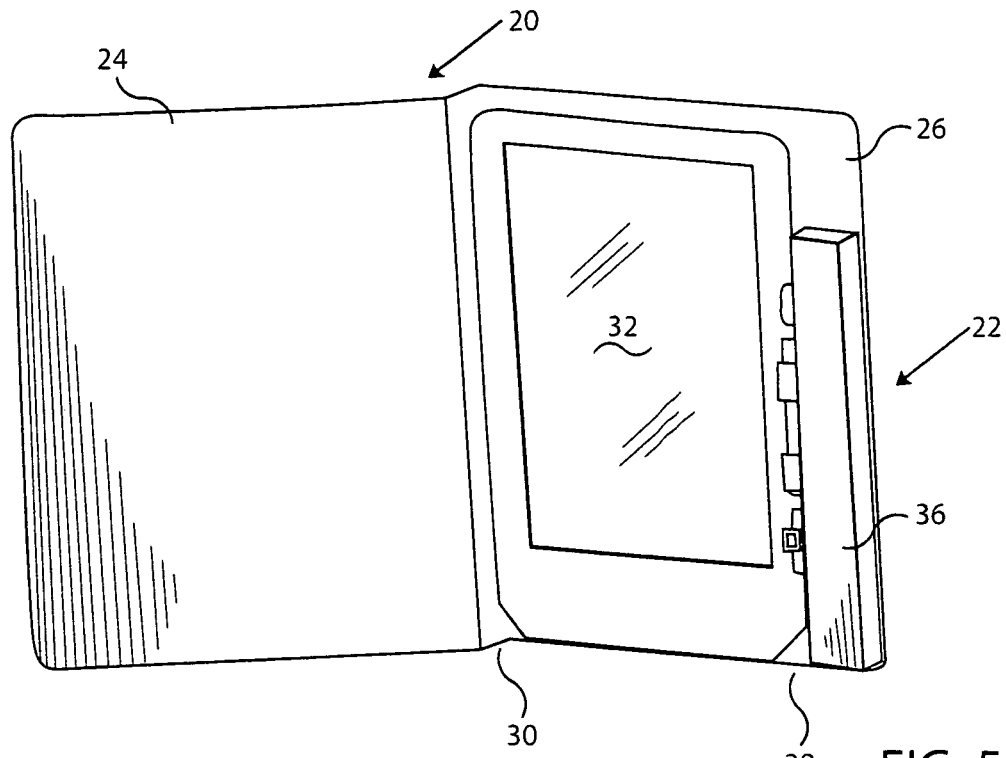
FIG. 5 is a perspective view of the cover of FIG. 3 with an e-book reader fully engaged with the example integrated button activator.

FIG. 4 is a perspective view similar to that of FIG. 3 which illustrates the engagement of a right edge of an example e-book reader 32 with the frame 28 of button activator 22. In this example, the e-book reader 32 continues to pivot down as indicated by arrow 34 until the left edge of the e-book reader 32 engages with the frame 30 and is slid into place as illustrated in FIG. 5. When the e-book reader 32 is in this position, it is firmly engaged with the frames 28 and 30 with its mechanical buttons along its right edge properly aligned with the button activator 22. The buttons of the e-book reader 32 are partially obscured in this view by a lid 36 of the button activator 22. In other non-limiting examples, an e-book reader can be engaged with cover 20 in other fashions, such as by sliding in from the top or bottom, snapping in, adhering to, etc.

Figure 6:
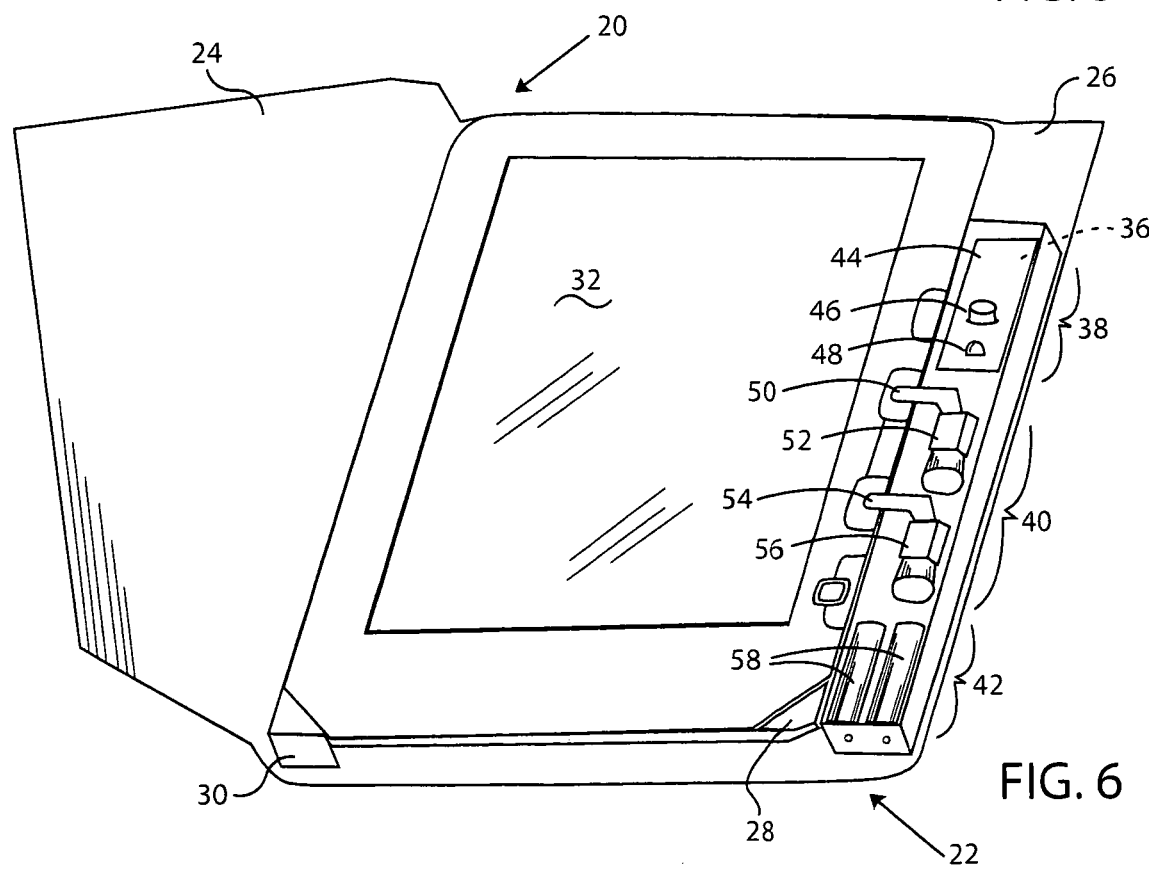
FIG. 6 is a perspective view of the cover of FIG. 6 with a lid portion of the example integrated button activator removed.

In FIG. 6, the cover 36 has been removed, as indicated by the broken line, to expose some of the internal components of button activator 22. The button activator 22 includes a controller zone 38, an actuator zone 40 and a power supply zone 42. The controller zone 38 includes a circuit board 44, a control button 46 and an LED indicator 48. The circuit board 44, by way of non-limiting example, can include a transceiver (or receiver) which can be paired or otherwise communicate with a transceiver (or transmitter) of a remote control device. The circuit board 44 may also include control logic for the actuators in the actuator zone. The actuator zone 40 includes a first actuator 50 coupled to a first motor 52 and a second actuator 54 coupled to a second motor 56. The actuators 50 and 54 are aligned with first and second mechanical switches, respectively, of the e-book reader 32. In this example, the first and second mechanical switches of the e-book reader are the "Page Forward" and "Page Back" buttons. The power supply zone 42, in this example, includes batteries 58. In other embodiments, a power supply may be used to power the button activator 22.

Figure 7:
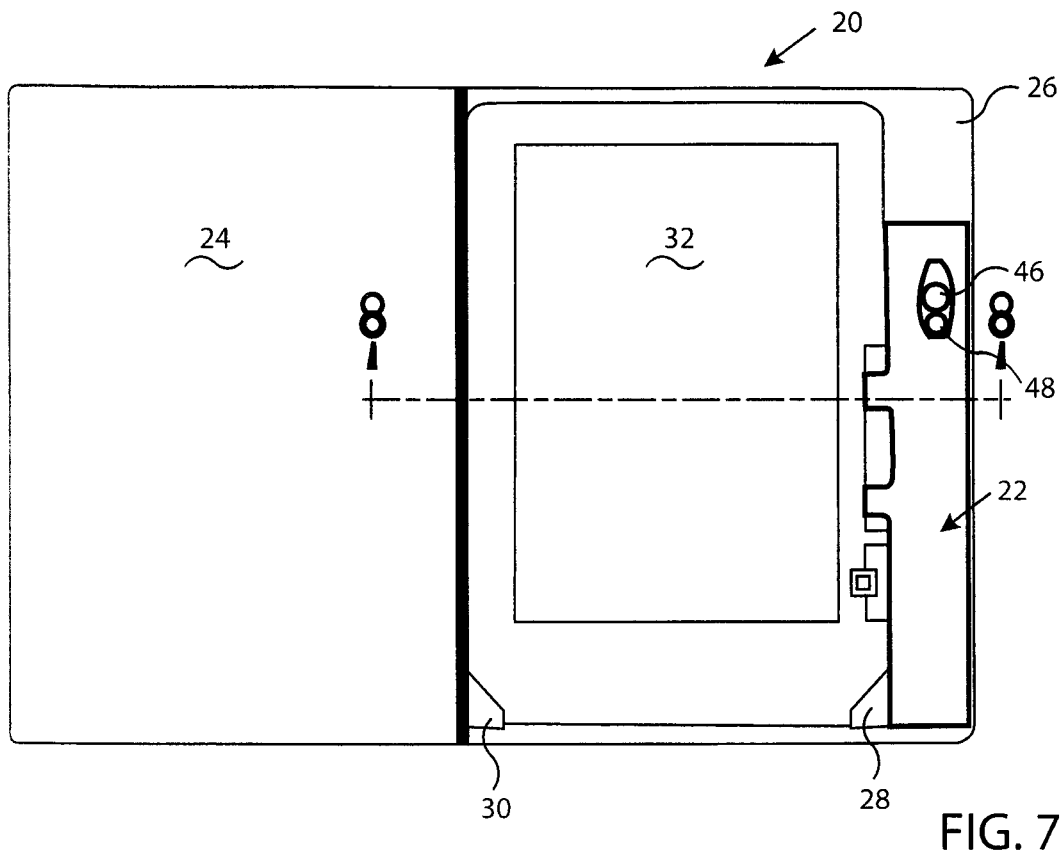
FIG. 7 is a top plan view of the cover of FIG. 2 in a fully open configuration.
Figure 8:
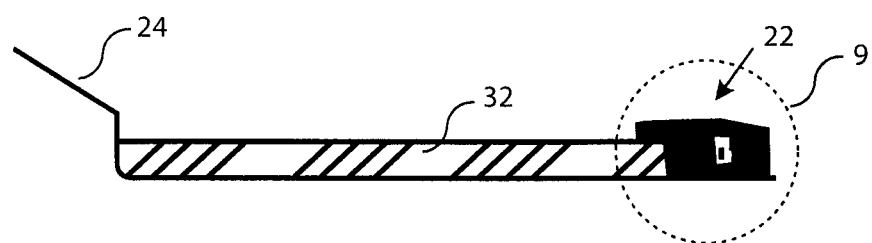
FIG. 8 is a cross-sectional view taken along line 8-8 of FIG. 7.
Figure 9:
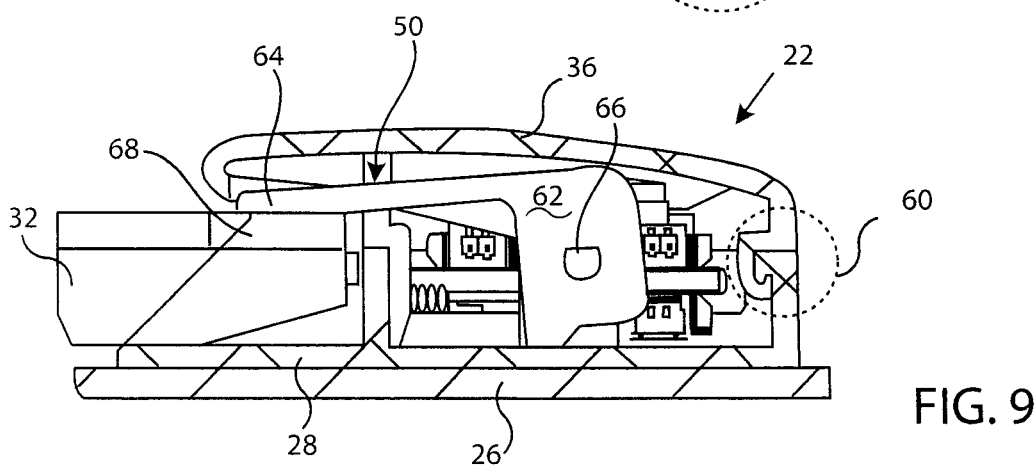
FIG. 9 is an enlargement of the portion of FIG. 8 encircled by line 9.

FIG. 7 is a top plan view of case 20 with e-book reader 32 engaged with frames 28 and 30. FIG. 8 is a cross-sectional view taken along line 8-8 of FIG. 7. FIG. 9 is an enlarged view of the portion of FIG. 8 encircled by broken line 9. In FIG. 9, the frame 28 is attached to inside of the back cover 26 by a suitable fastener such as an adhesive or a mechanical fastener. Cover 38 is hinged to frame 28 at a junction 60. Actuator 50 has a fulcrum portion 62 and an arm portion 64. The actuator 50 can be rotated on an axle 66 coupled to motor 52 (not seen in this view). The tip of arm portion 64 may contact and press on a button 68 of e-book reader 32. As will be discussed in greater detail subsequently, the motor 52 can cause the actuator 52 to be rotated between a neutral and a button-press position. As used herein, a "neutral position" is a position where an actuator is not exerting a pressing force on a real or virtual button that is sufficient to be considered a button push, and a "button-press position" is a position where an actuator is exerting a pressing force on a real or virtual button sufficient to be considered a button push.

The examples of FIGS. 2-9 provide a wrap-around cover 20 which protects an e-book reader while providing mechanical button-pushing capabilities. Other examples may not include a wrap-around cover and/or may not mechanically activate buttons of an e-book reader. For example, a button actuator can be clamped, glued, or otherwise directly attached to an e-book reader without the need for a cover. Also, there are many other examples of wrap-around covers which can be used for e-book readers, including alternate physical and non-physical e-book interfacing configurations.

Figure 1A:
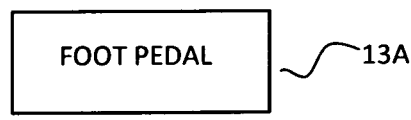
FIG. 1A is a representation of a foot pedal 13A which, by way of non-limiting example, can serve as a remote control device 13 of FIG. 1.
Figure 10:
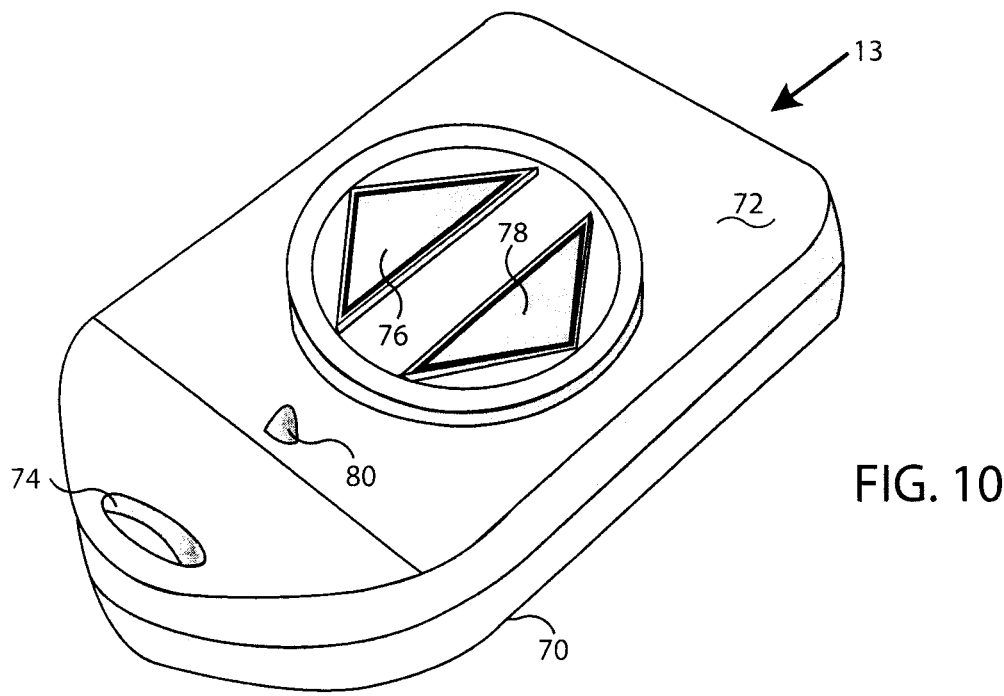
FIG. 10 is a perspective view of an example remote control.

FIG. 10 is an example of a remote control device 13 of FIG. 1. In this example, remote control device 13 is configured as a FOB which can be carried on a keychain or the like. In this regard, it is similar in configuration to an electronic car door opener. Of course, this configuration is just one of many examples suitable for remote control device 13. By way of a further non-limiting example, a remote control device 13 of FIG. 1 can be a foot pedal 13A for use by musicians or transcriptionists as illustrated in FIG. 1A. Another non-limiting example is that of a handicap-accessibility switch used by a person with limited hand/finger dexterity (e.g., those commercially available from Ablenet, Inc.).

In the example of FIG. 10, remote control device 13 includes a lower casing 70, an upper casing 72, a keychain aperture 74, a pair of buttons 76 and 78, and an indicator LED 80. In this example, the buttons 76 and 78 are shaped as arrowheads to indicate a forward page turn and a back page turn.

Figure 11:
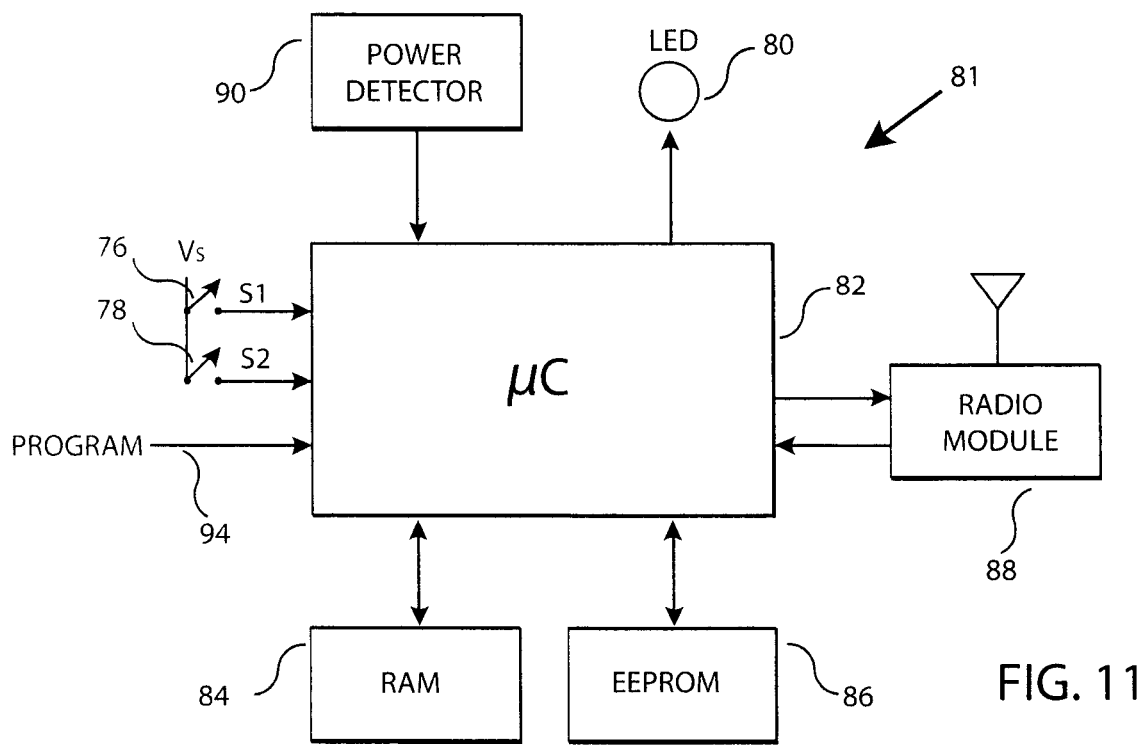
FIG. 11 is an example block diagram of the example remote control of FIG. 10.

FIG. 11 is an example block diagram of the electronic circuitry 81 of the remote control device 13 of FIG. 10. In this example, electronic circuitry 81 includes a microcontroller 82 coupled to the buttons (e.g. switches) 76 and 78, a RAM 84, an EEPROM 86, a radio module 88, a power detector 90, and indicator LED 80. It should be noted that the block diagram of FIG. 11 is illustrating functional blocks and that the components may be arranged differently. For example, the RAM 84 and EEPROM 86 may be integrated into the microcontroller 82 and the power detector 90 may be integrated into the radio module 88. Furthermore, there may be buffering and other intermediate circuitry between, by way of example and not limitation, the buttons 76 and 78 and the microcontroller 82. These and other design variants will be appreciated by those of ordinary skill in the art.

The example remote control device 13 may also include other inputs, not shown, such a 3.5 mm jack to receive alternate switch closures, or other forms of electrical signals, from a user-selected unit. These alternate switch closures may replace, or augment, for example, switches 76 and 78. For example, the aforementioned jack, or other input port, can be used to allow a standardized interface, such as electric foot pedal used by musicians, to provide electrical inputs to the remote control device 13. By way of further example, there are a number of standardized interfaces designed for those with disabilities which can also benefit by being coupled to the remote control device 13.

The radio module 88 may be configured to operate using, for example, the IEEE 802.15.4 protocol. The IEEE 802.15.4 protocol is a standard which specifies the physical layer and media access control for low-rate wireless personal area networks (LR-WPANs). A typical range for this protocol is about 30 feet and the transfer rate is about 250 Kbits/sec. Lower bit rates can be selected with a corresponding reduction in power consumption. The IEEE 802.15.4 protocol allows for a low cost, low power consumption master/slave communication link 16 between remote control device 13 and button activator 14 (see FIG. 1) with built-in retry and collision avoidance protocols.

Preferably, each remote control device 13 will have a unique identifier (typically 64 bits) in accordance with the IEEE 802.15.4 specification. The unique identifier may be stored in EEPROM 86 and can be loaded into the radio module 88 by the microcontroller 82 upon power-up. This will allow a remote control device 13 to be uniquely paired with a corresponding button activator 14. In other examples, a remote control device 13 may be paired with multiple slave units for, for example, musical applications. The EEPROM 86 can be programmed through a port 94 at, for example, the time of production. As another non-limiting example, the EEPROM 86 can be user-programmable.

Figure 12:
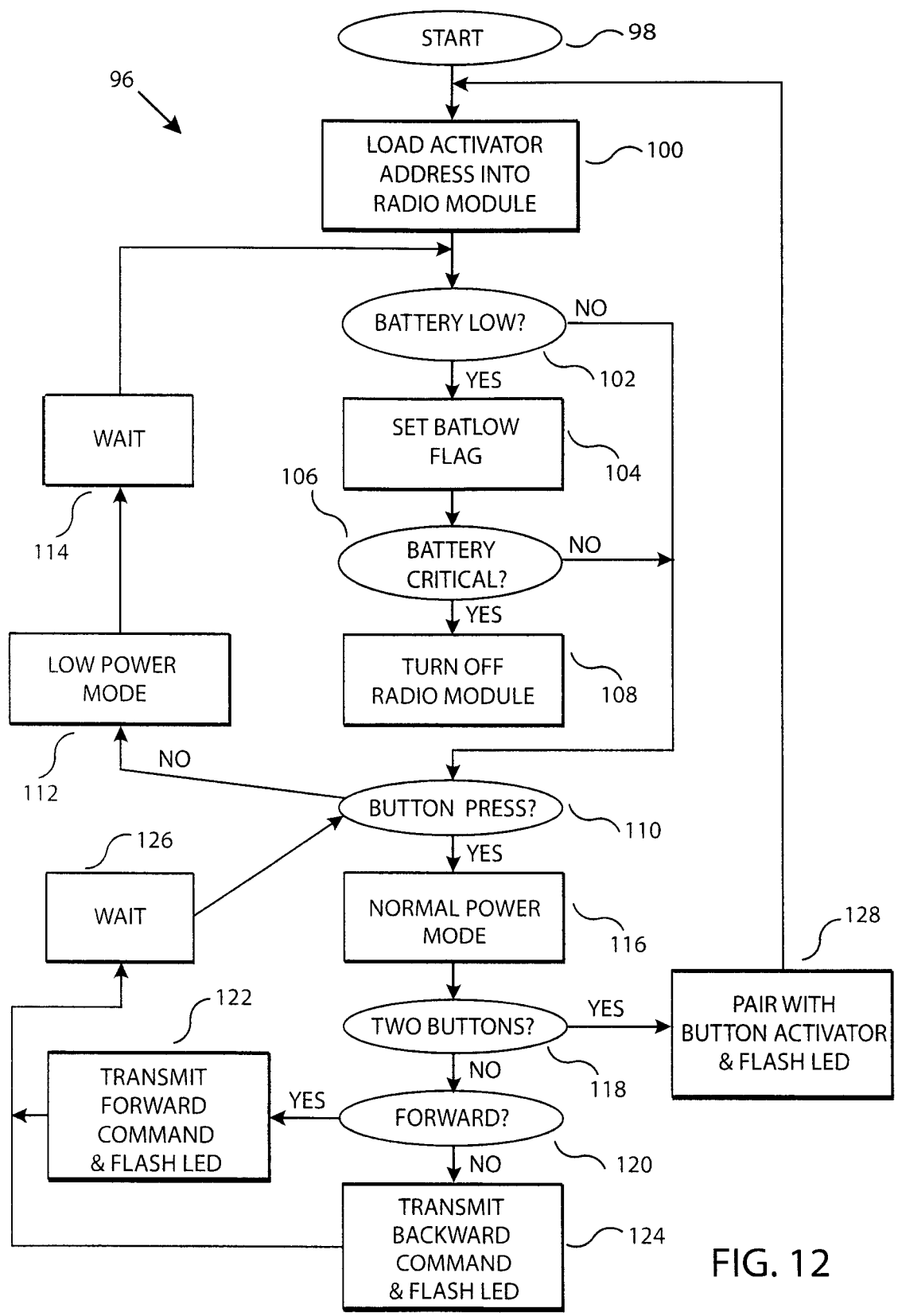
FIG. 12 is a flow diagram of an example process which may be implemented by the example block diagram of FIG. 11.

FIG. 12 is a flow diagram of an example process 96 which may be implemented on the apparatus of FIG. 11. Instructions for microcontroller 82 to implement process 96 may be stored, for example, in the EEPROM 86. Process 96 starts at 98 and, in an operation 100, the address of the button activator 14 (the "slave" in this example) is loaded into radio module 88. Next, in an operation 102, it is determined whether the battery is low on power by, for example, monitoring the power detector 90. If battery power is low, a BATLOW flag is set in an operation 104. If battery power is critically low, as determined by operation 106, the radio module 88 is turned off in an operation 108, effectively disabling the remote control device 13. If there is sufficient battery power to operate normally, process control is then given to operation 110 which looks for a press on button 76, button 78, or both. If a button press is not detected in operation 110, an operation 112 puts the remote control device 13 into a low power mode to conserve energy and then into a timed wait period in an operation 114. After the wait period has elapsed, process control is returned to operation 102.

If operation 110 does detects a push of button 76, 78 or both, an operation 118 determines whether both buttons have been pushed, indicating that the remote control device 13 is to enter a pairing mode, in this example. If both buttons have been pressed, the remote control device 13 is paired with button activator 14 and LED 80 is flashed appropriately in an operation 128. Operational control is then returned to operation 100.

If operation 110 detects the push of only one button, an operation 120 determines which button has been pushed. If the forward button has been pushed, the radio module is caused to transmit a "Page Forward" signal in an operation 122, with the LED 80 being flashed appropriately. If the back button has been pushed, the radio module is caused to transmit a "Page Back" signal in an operation 124, with the LED 80 being flashed appropriately. After transmitting either signal, the process waits as indicated at 126 and then process control is returned to operation 110.

Figure 13:
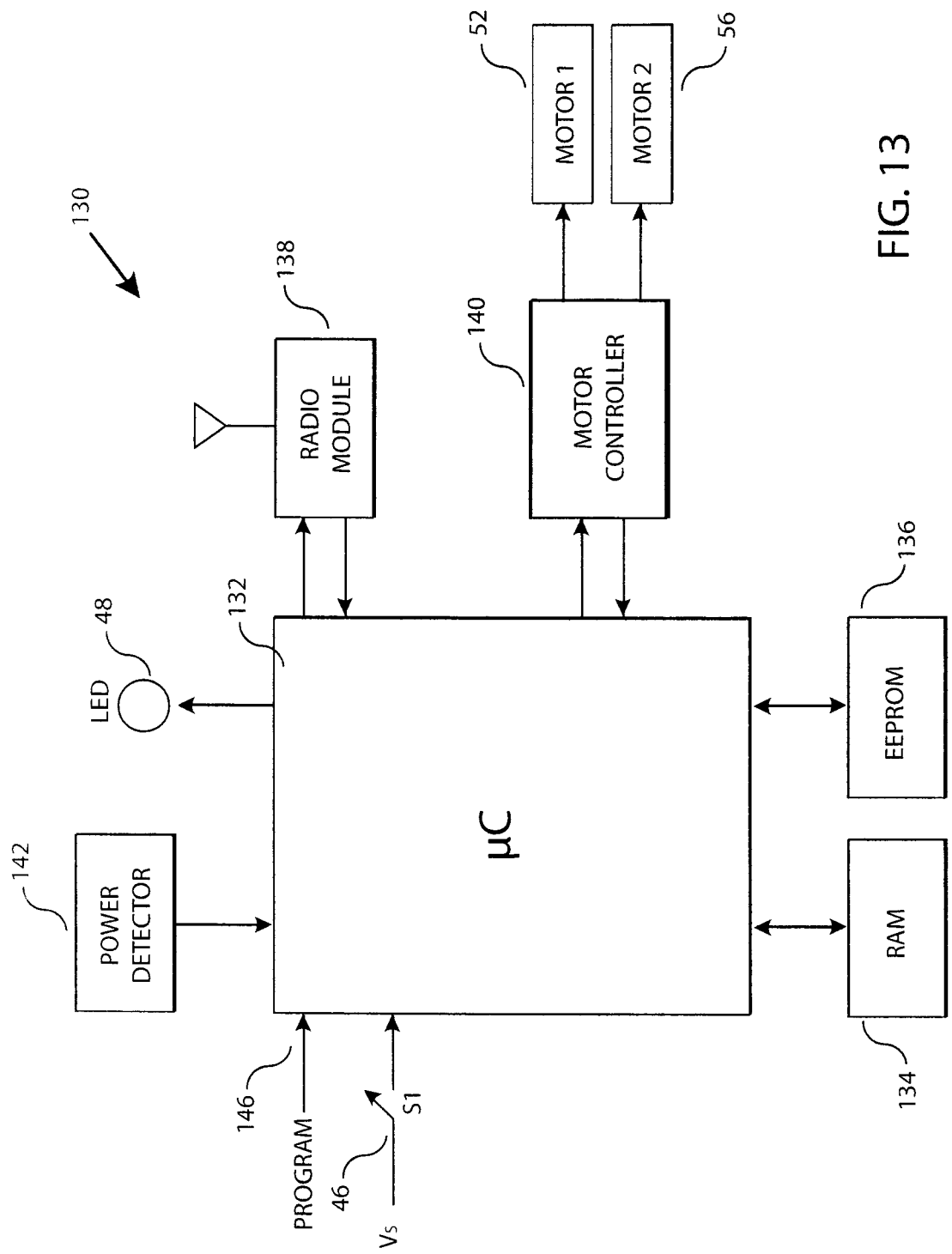
FIG. 13 is an example block diagram of the example button activator of FIG. 2.

FIG. 13 is an example block diagram of electronic circuitry 130 of the button activator 14. In this example, electronic circuitry 130 includes a microcontroller 132 coupled to the buttons (e.g. switch) 46, a RAM 134, an EEPROM 136, a radio module 138, a power detector 142, and the indicator LED 48. A motor controller 140 is coupled between the microcontroller 132 and the motors 52 and 56. It should be noted that the block diagram of FIG. 13 is illustrating functional blocks and that the components may be arranged differently. For example, the RAM 134 and EEPROM 136 may be integrated into the microcontroller 132 and the power detector 142 may be integrated into the radio module 138 or the motor controller 140. Furthermore, there may be, by way of example and not limitation, buffering and other intermediate circuitry between the button 46 and the microcontroller 132. These and other design variants will be appreciated by those of ordinary skill in the art.

The radio module 138, in this example, is also configured to operate with the IEEE 482.15.4 protocol. Preferably, each button activator 14 will have a unique identifier (typically 64 bits). The unique identifier may be stored in EEPROM 86 and can be loaded into the radio module 138 by the microcontroller 132 upon power-up. This will allow a button activator 14 to be uniquely paired as a "slave" with a corresponding "master" remote control unit 13. The EEPROM 138 can be programmed through a port 146 at, for example, the time of production.

Figure 14:
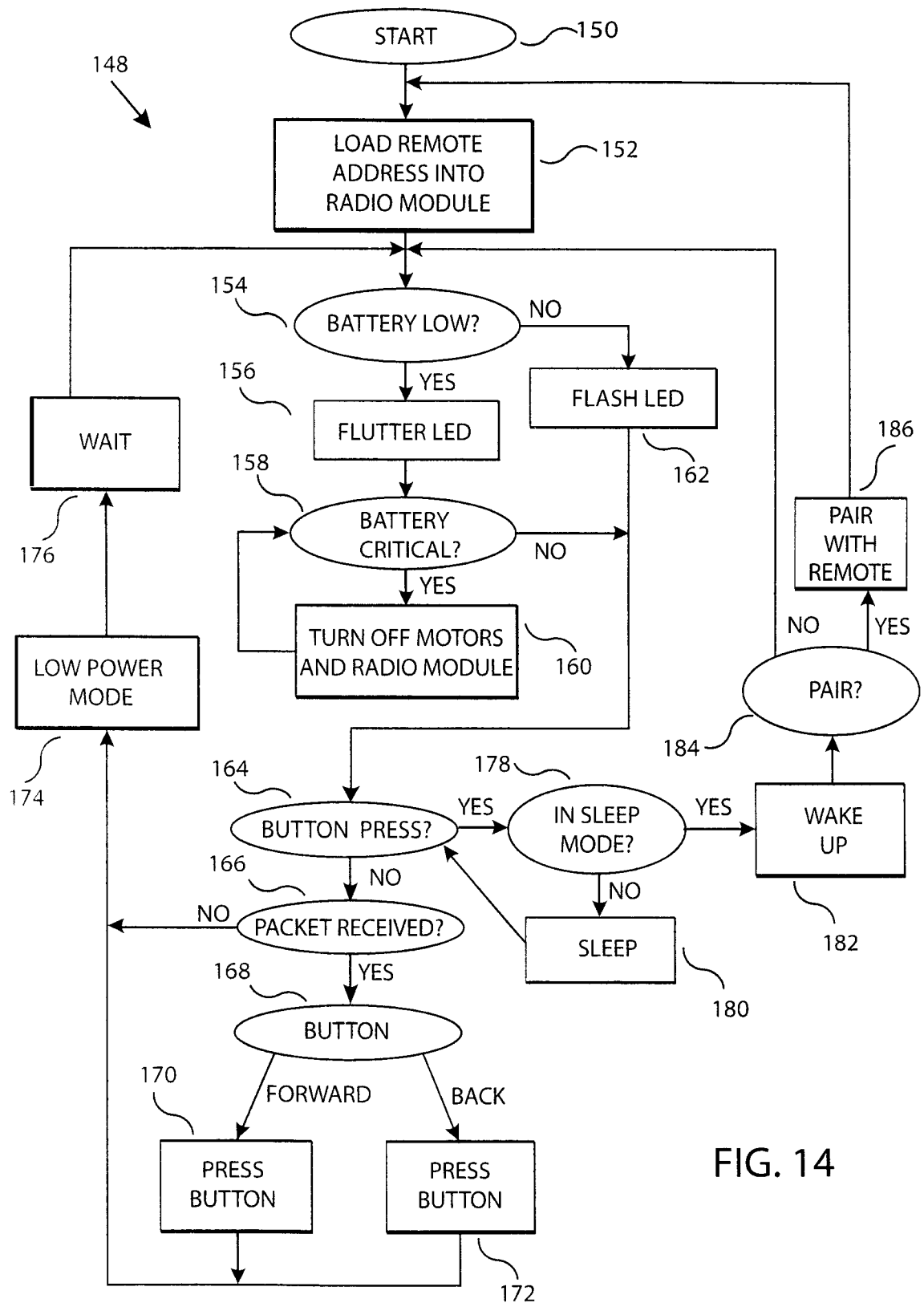
FIG. 14 is a flow diagram of an example process which may be implemented by the example block diagram of FIG. 13.

FIG. 14 is a flow diagram of an example process 148 which may be implemented on the apparatus of FIG. 13. Instructions for microcontroller 132 to implement process 148 may be stored, for example, in the EEPROM 136. Process 148 starts at 150 and, in an operation 152, the address of the paired remote control device 13 is loaded into the radio module 138. Next, in an operation 154, it is determined if the power level of the battery is low. If so, the LED 48 is "fluttered" in an operation 156. If the power level of the battery is critically low as determined by operation 158, the motors 52 and 56 and the radio module 138 are turned off in an operation 160, essentially shutting down the button activator 14. If battery power is sufficient to support operation, the LED either flashes by operation 162 or flutters by operation 156 and operational control is turned over to operation 164

If operation 164 does not detect a pressing of button 46, operation 166 determines whether a packet addressed for the button activator 14 has been received. If not, the button activator 14 enters a low power mode in an operation 174 and then a wait mode in operation 176 before returning to operation 154.

If operation 166 determines that an appropriate packet has been received, an operation 168 determines which button is to be pressed. If the "Page Forward" button is to be pressed, a press button operation 170 is activated. If the "Page Back" button is to be pressed, a press button operation 172 is pressed. Operational control is then given to operation 174.

If a button press of button 46 was detected in operation 164 it is determined whether the button activator 14 is in a sleep mode in an operation 178. If it is not in a sleep mode, an operation 180 puts the button activator 14 into a sleep mode to await another button press in operation 164. If operation 178 determines that the button activator is currently in a sleep mode, it is woke up in a wake up operation 182. An operation 184 then determines if the button activator 14 is to be paired. If so, the button activator 14 is paired with the remote control device 13 in an operation 186 and process control is returned to operation 152. If the button activator 14 is not to be paired, operational control is returned to operation 154.

Figure 15:
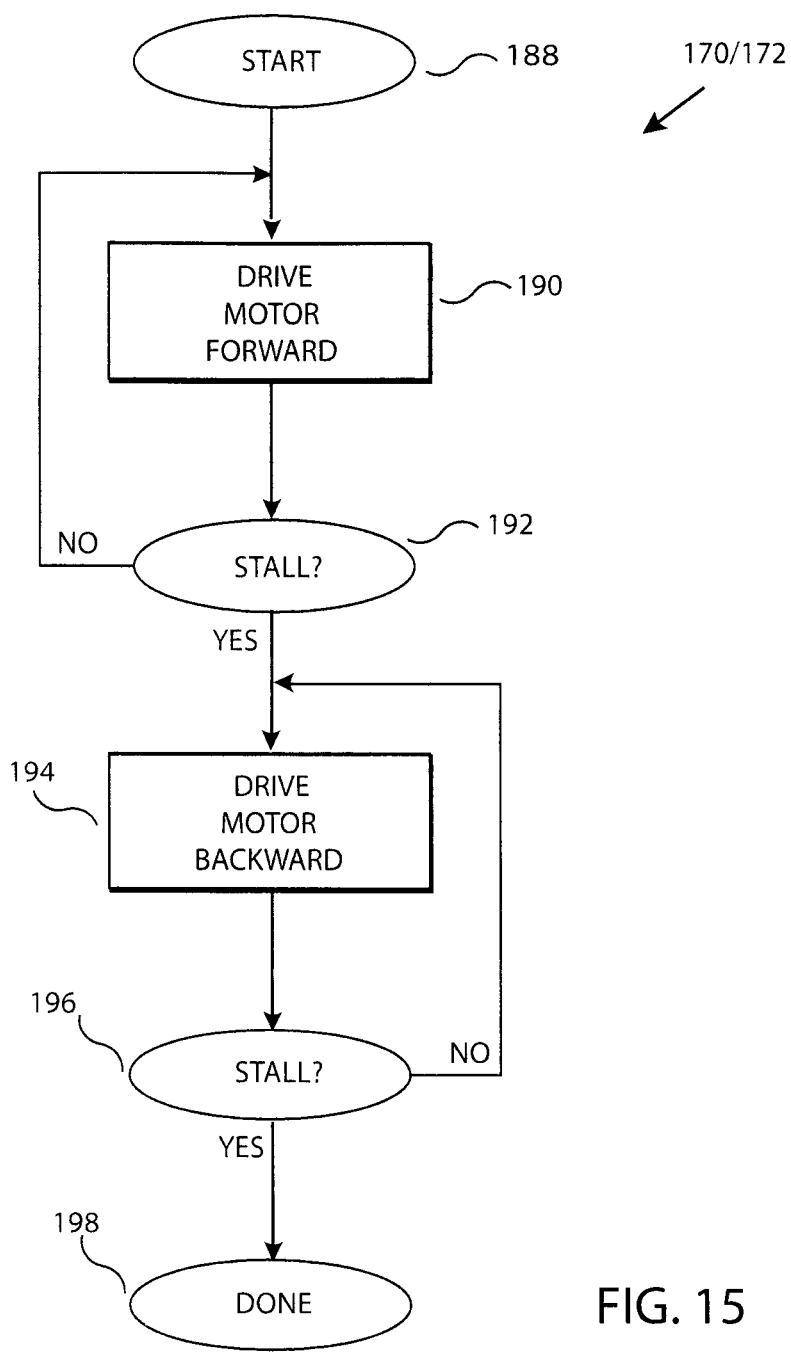
FIG. 15 is a flow diagram of an example process to implement the PRESS BUTTON operation of FIG. 14.

FIG. 15 is a flow diagram illustrating the PRESS BUTTON 170/172 operations of FIG. 14. The processes 170/172 start at 188 and, in an operation 190, the appropriate motor is driven in a forward direction. Then in an operation 192, it is determined whether the motor has "stalled", e.g. can no longer rotate its shaft. This is typically detected by a surge of current being drawn by the motor. If there is no stall, the motor continues to drive the motor forward in operation 190. If a stall condition is detected by operation 192, an operation 194 drives the motor in the reverse or "backward" direction until a stall is detected in an operation 196. The process 170/172 is done at 198.

In another example, button "push back" from an e-book reader button can be used to eliminate the need to reverse the motor as described above. That is, in many cases the button on an e-book reader is spring-loaded to return itself to its unpressed or neutral position. With such examples, the operations 194 and 196 may be skipped or eliminated.

In the examples set forth above, and in other examples, it may be preferable to keep the circuit designs for the remote control device 13 and the button activator as similar as possible. For example, the same microcontrollers and radio modules can be used to allow a sharing of the firmware stored in their EEPROMS. Suitable microcontrollers include the PIC18F25K20T-I/SS processor and suitable radio modules include the MRF24J40MA-I/RM RF module, both available from Microchip, Inc. A suitable motor driver is the MPC17531A motor driver available from Freescale, Inc. Of course, there are many substitutes and equivalents for the components described above. For example, the microcontroller can be replaced with other technologies including microprocessors, state machines, discrete logic, and other forms of digital processors.

Since both the remote control device 13 and the button activator 14 in the examples set forth above are battery powered, preferred embodiments include power management and power level indications. Remote control device 13 can be powered by, for example a 20 mm×3.2 mm coin battery model #CR2032 which has a 22 mAh capacity. Button activator 14 can be powered, for example, by two AAA batteries.

By way of further examples, when the battery on the remote control device 13 is at an acceptable level, the LED 80 can be flashed slowly during radio communication. When a low battery power level is detected, the LED 80 can be "fluttered", e.g. blinked rapidly. Similarly, when battery power is at an acceptable level in the button activator 14, the LED 48 may be flashed slowly to show that it is powered and "listening" for a packet from its paired remote control device 13. If a low battery level is detected, the LED can be caused to flutter. In other examples, fewer or no LEDs can be used, or more LEDs can be used to provide feedback to a user. Multiple outputs can be displayed on a single LED with, for example, software controlled "OR-wired" processes. In still further non-limiting examples, other display technologies, including audio, visual and tactile display can be used.

Besides indicating battery power levels, preferred embodiments may employ power management techniques to reduce power consumption whenever possible. Since radio communications are a major source of power consumption, the radio modules a preferably put into a sleep mode on a regular basis and the microcontroller should be put into a low-power "idle" mode when not being used. By way of example, the radio modules described above can be programmed to wake up the radio module and then the microcontroller after a programmable time period.

The motor controller described above also has an analog-to-digital (A/D) channel which can be used to periodically monitor the battery voltage. This can be used to alert the user of low battery conditions. Preferably, the motor controller also has the capability of entering "deep sleep" to conserve battery life.

As noted previously, the remote control system 10, in the described examples, may implement the IEEE 802.15.4 radio communication protocols with the remote control device 13 being the master and the button activator 14 being the slave. In other examples, other protocols and other relationships may be implemented. In the current example, the remote control device 13 initiates all communications and the button activator 14 "listens" for command packets from the remote control device 13 and will only respond when addressed directly by its "paired" remote or to a "pairing" request broadcast by the remote control device 13 when the button actuator is in a "paring" mode.

The button activator 14 or "slave" device, in this example, will listen during a 20 millisecond window every 200 milliseconds. After the 20 millisecond communication window, the radio and microcontroller will enter low-power modes. This power management technique reduces the "slave" radio power consumption to approximately 10% of that consumed by continuous operation.

The remote control device 13 or "master" device, in the example, will only transmit when a user presses its buttons. Otherwise, its radio module and microcontroller will be in low-power modes. When a button is pressed, the "master" device will transmit a series of 3 command packets every 5 milliseconds until the "slave" device responds with an "ACK" or 200 milliseconds expire. Therefore, the radio module of the "master" can operate either as a transmitter or a transceiver, it being understood that a transmitter is a subset of a transceiver. Likewise, the radio module of the "slave" can operate as either a receiver or as a transceiver, it being understood that a receiver is a subset of a transceiver.

Preferably, the remote control device 13 only transmits once every second. If a user presses buttons more than once per second, they may be queued for transmission at a rate of once per second. These power management techniques on the remote control device 13 reduce power consumption to 20% of continuous operation power consumption.

The motor controller described above is capable of driving two direct current (DC) motors. Only one of the motors should be run at a time. When a command is received to "cycle" a button on a digital electronic display device, the microcontroller will drive the appropriate motor forwardly while monitoring the motor current as was described with respect to FIG. 15. When the current exceeds a predetermined limit (e.g. a stall current of 200-300 mA), the microcontroller will back off the motor and then drive it in reverse until the "stall" current is detected in the other direction. Preferably, the radio module is in a low-power mode while the motor is driven.

By way of example, the microcontroller of the button activator 14 may use software-generated pulse width modulation (PWM) waveforms when driving the motors both for the purpose of power savings and also to "ramp" up the motor speed to extend the life of the motors. A PWM of approximately 100 kHz may be desirable for smooth motor operation. The full speed PWM may have a 50% or greater duty cycle.

To produce the desired PWM, the microcontroller of the button activator 14 may be operated at 16 MHz to produce the PWM waveform and to interleave instructions to read the A/D channel to monitor battery voltage. The A/D channel is preferably configured for continuous operation using a programmable timer such that the firmware needs only to monitor the results registers once the A/D is started. In alternate examples, a hardware PWM may be employed.

In the example above, when the two buttons on the remote control device 13 are pressed simultaneously for a period of time (e.g. 4 seconds) the remote control device 13 is put into a pairing mode. On the other hand, when the button on the button activator 14 is pressed for a period of time (e.g. 5 seconds) the button activator 14 enters a "deep sleep" mode as was described with respect in FIG. 14. Pressing the button on the button activator 14 when it is in deep sleep for a period of time (e.g. 2 seconds) will wake it from the deep sleep. If the button is continued to be held for a longer period of time (e.g. 5 seconds) the button activator 14 enters the "pairing" mode.

During pairing, only the remote control device 13 and the button activator 14 should be in pairing mode within the range of their radio modules. The remote control device 13 periodically sends out a "pairing" request packet. When the button activator 14 receives the pairing request packet, it will transmit a "pairing" response packet. When the remote control device 13 receives the "pairing" response packet, it will send a second "pairing" request packet directly to the button activator 14 (not broadcast). Once the button activator 14 receives the "pairing" request packet with its address, it is paired with the remote control device 13 and stores the address of the remote control device 13 in its EEPROM, overwriting any previously stored address.

In the foregoing examples, rotary DC motors were employed due to price and power considerations. However, as used herein, the term "motor" includes any electromechanical transducer including linear solenoids, rotary solenoids, piezoelectric motors, "muscle wire" nitinol memory wire, etc.

Figure 16A:
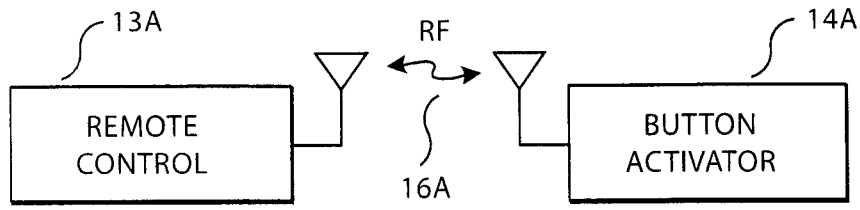
FIGS. 16A-16E illustrate various examples of communication between example remote controls and example button activators.
Figure 16B:
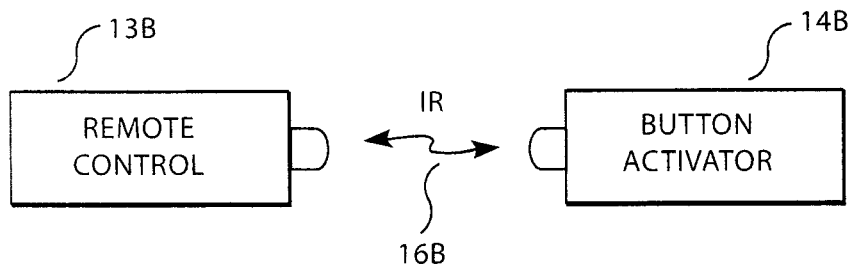
Figure 16C:
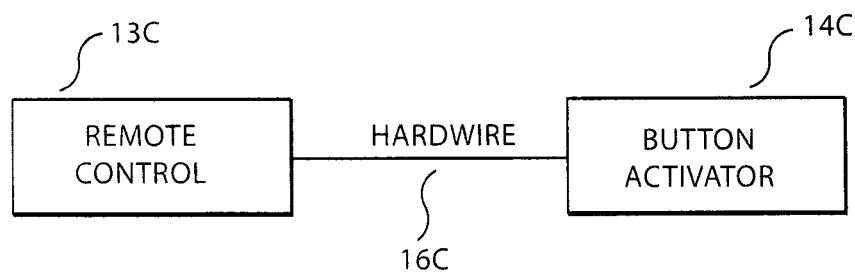
Figure 16D:
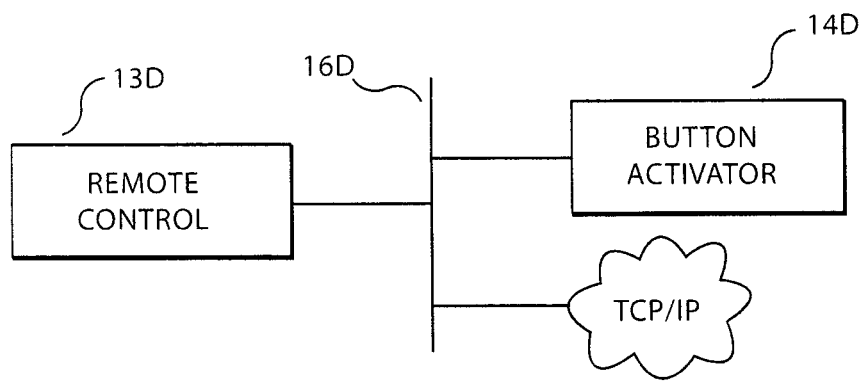
Figure 16E:
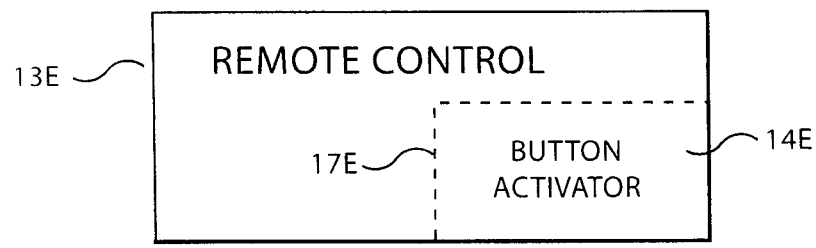

FIGS. 16A-16E illustrate various interfaces 16 between remote control device 13 and button activator 14. In FIG. 16A, a remote control device 13A communicates with a button activator 14A by a radio frequency (RF) interface 16A. The RF interface can be of a variety of protocols, including Wi-Fi, Bluetooth, etc. In FIG. 16B, a remote control device 13B communicates with a button activator 14B by an infrared (IR) interface 16B. In FIG. 16C, a remote control device 13C communicates with a button activator 14C by a hardwire interface 16C, e.g. a wire, cable or electrical connector. In FIG. 16D, a remote control device 13D communicates with a button activator 14D by a network interface 16D. The network interface 16D (which can be wired or wireless) can include a TCP/IP network connection, e.g. the Internet. In FIG. 16E, a remote control device 13E communicates with a button activator 14E by an integrated interface 16E by becoming a part of the remote control device.

Figure 17A:
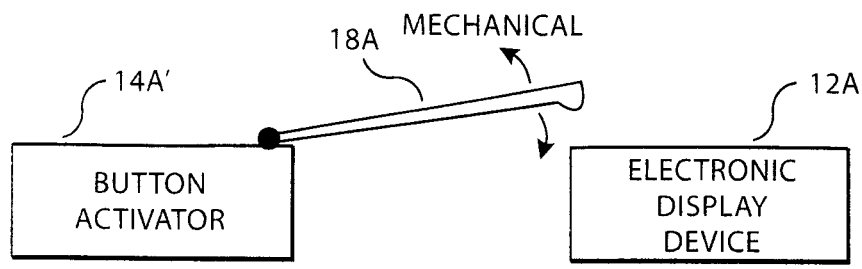
FIGS. 17A-17E illustrate various examples of communication between example button activators and example electronic display devices.
Figure 17B:
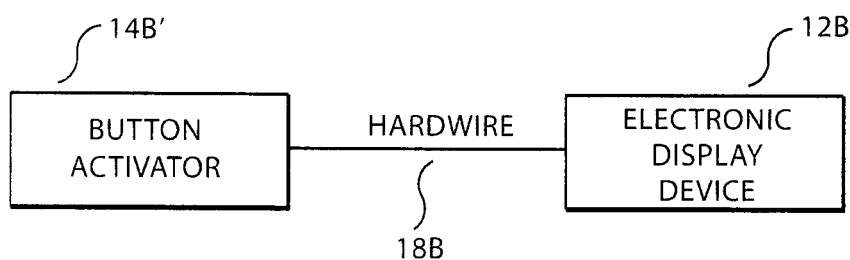
Figure 17C:
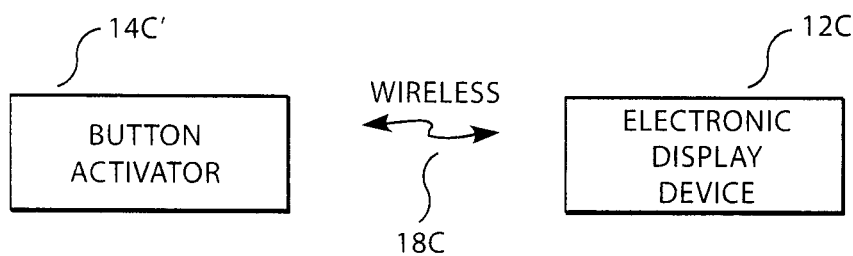
Figure 17D:
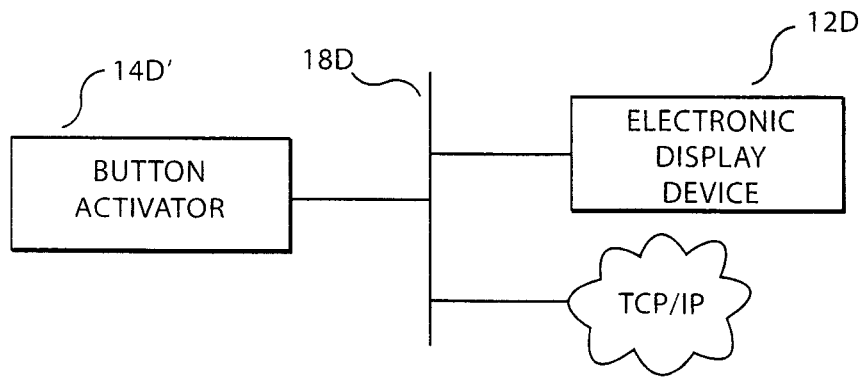
Figure 17E:
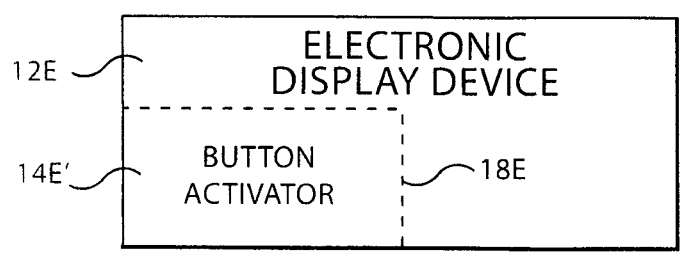

FIGS. 17A-17E illustrate various interfaces 18 between button activator 14 and digital electronic display device 12. In FIG. 17A, a button activator 14A' communicates with a digital electronic display device 12A by a mechanical interface 18A. In FIG. 17B, a button activator 14B' communicates with a digital electronic display device 12B by a hardwire interface 18B, e.g. a wire, cable or electrical connector. In FIG. 17C, a button activator 14C' communicates with a digital electronic display device 12C by a wireless interface 18C. The wireless interface may be electromagnetic (such as RF or IR signals), acoustic, etc. In FIG. 17D, a button activator 14D' communicates with a digital electronic display device 12D by a network interface 18D. The network interface 18D (which can be wired or wireless) can include a TCP/IP network connection, e.g. the Internet. In FIG. 17E, a button activator 14E' communicates with a digital electronic display device 12E by an integrated interface 18E by becoming a part of the electronic display device.

As noted above, the interface between a button activator and an electronic display device may be mechanical, hardwired, wireless, networked or integrated, by way of non-limiting examples. As a further example of a hardwired interface of FIG. 17b is an interface through an input/output (I/O) port of an e-book reader. For example, the Apple iPad/iPhone® ("iPhone OS" or "iOS") devices (which can serve as e-book readers) include a docking port along a bottom edge. In an embodiment, logic is provided which provides control signals to an iPhone OS device via its docking port. This may be facilitated, by way of non-limiting example, by interfacing with an Apple NSNotification object (which is a form of notification dispatch table) using Apple's EAAccessory Framework API.

With the non-limiting example set forth above, a forward button pressed on, for example remote control device 13, may cause a receiving circuit to develop a packet for the iPhone OS device docking port with a control command or signal, e.g.:

[[NSNotificationCenter defaultCenter] postNotificationName @ "swipe left" object: self]

Continuing with this non-limiting example, a reverse or "backward" button pressed on, for example remote control device 13, may a receiving circuit to develop a packet for the iPhone OS device docking port with a control command or signal, e.g.:

[[NSNotificationCenter defaultCenter] postNotificationName @ "swipe right" object: self]

An advantage of using an electronic interface between a button activator 14B' and an electronic display device 12B of FIG. 17b is that electromechanical components, such as motors or other actuators, can be eliminated, resulting in lower costs, lower power consumption and less wear on the button activator. It will further be appreciated that the buttons of the iPhone OS device are "activated", in this example, without ever being physically pressed.

Figure 18:
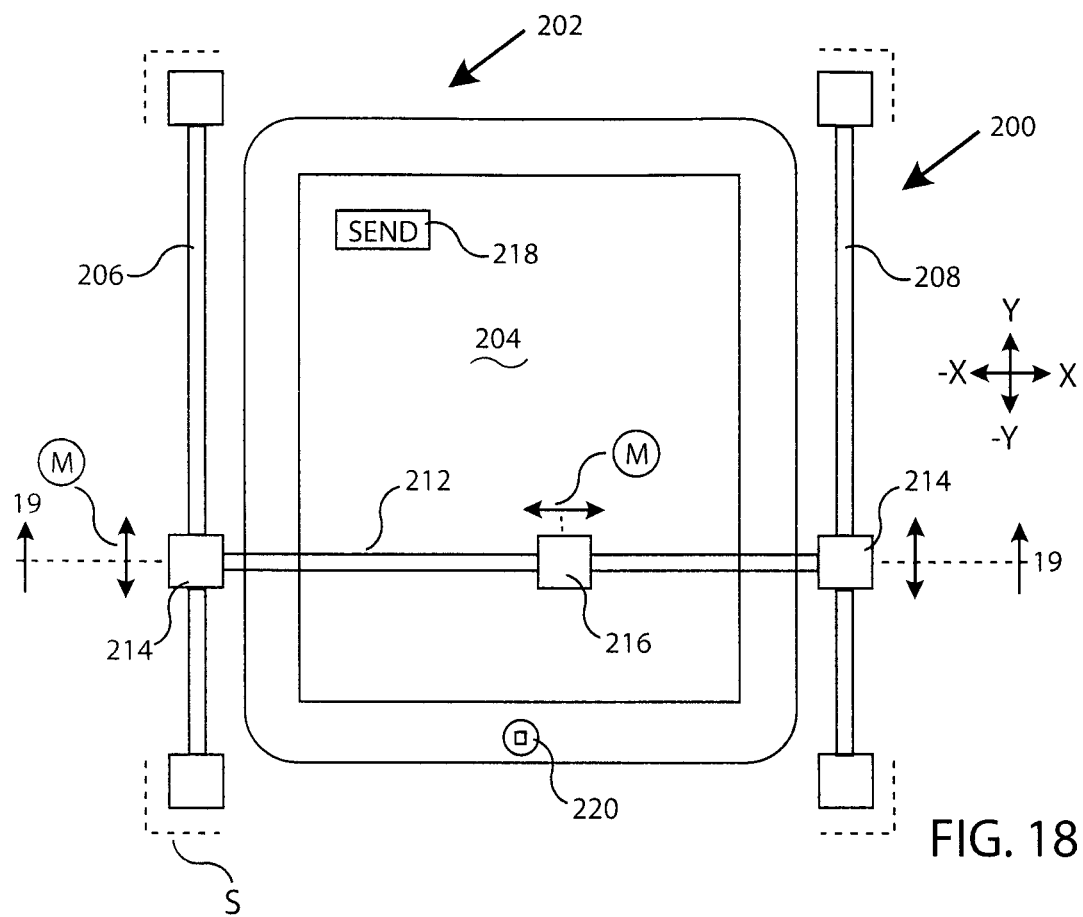
FIG. 18 is a top plan view of an example button activator suitable for use with digital electronic display devices having touch screens.
Figure 19:
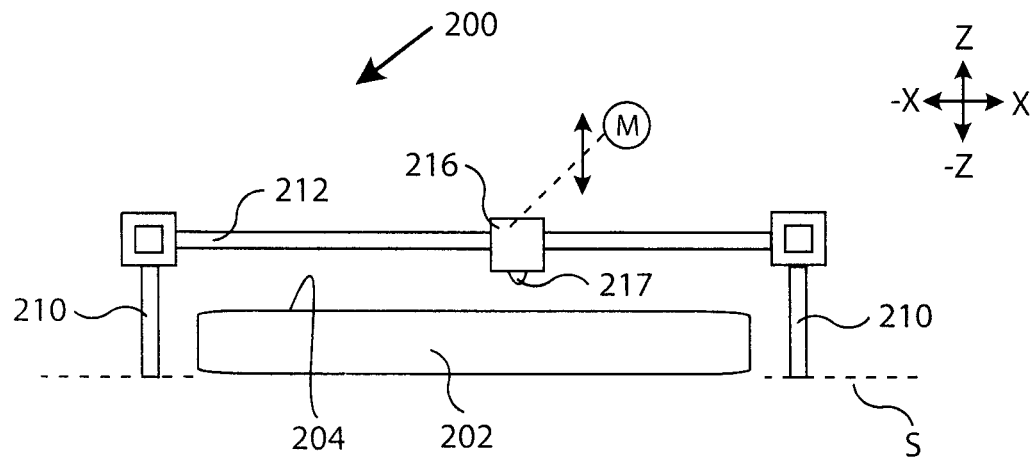
FIG. 19 is a cross-sectional view taken along line 19-19 of FIG. 18.

FIG. 18 is a top plan view of an example button activator 200 suitable for use with a digital electronic display device 202 having a touch screen 204 such as an iPad tablet computer. FIG. 19 is a cross-sectional view taken along line 19-19 of FIG. 18. With respect to FIGS. 18 and 19, the example button activator 200 includes a pair of rails 206 and 208 supported over a support surface S by posts 210. A rail 212 extends between sliders 214 such that rail 212 may slide along rails 206 and 208 in a ±Y direction. A carriage 216, which includes a protrusion 217 on its bottom side, is engaged with rail 212 such that it may slide along line rail 212 in a ±X direction. The carriage can also move in a ±Z direction between a neutral and button press position wherein the protrusion 217 engages the touch screen 204. It should be noted that the X, Y and Z dimensions are generally orthogonal in this example. Movement in the X, Y and Z directions is accomplished by a number of motors M which are preferably under microcontroller control.

In operation, the carriage 216 can be positioned over a virtual button on touch screen 204, such as a virtual button 218 labeled "SEND", or over a mechanical button, such as button 220 by moving the carriage 216 in the X and/or Y directions. A button press can be effectuated by moving the carriage 216 in the X and Y directions when it is in its "neutral" position until it is aligned with the button, and then moving the button in the −Z direction to press the button.

It should be noted that the button activator 200 can also make gestures on the on the touch screen by moving the carriage 216 in X and/or Y directions while it is still engaged with the touch screen 204. More complex gestures can be made by providing additional, independently controllable carriages.

Figure 20:
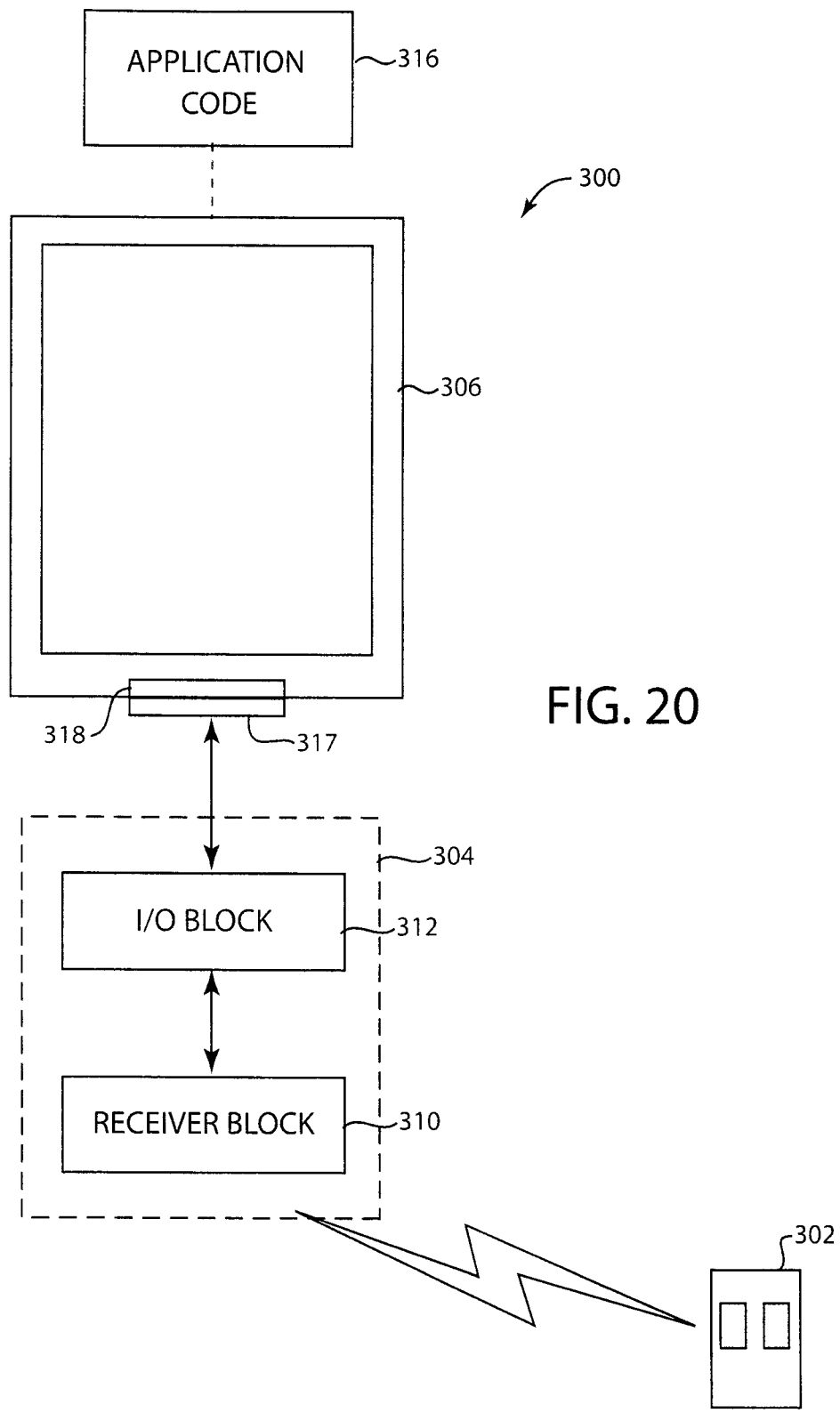
FIG. 20 is a block diagram illustrating an example of a remote control system for providing page turning capability using an electronic interface to a digital electronic display device.

FIG. 20 is a block diagram illustrating an example of one embodiment of a remote control system 300 for providing page turning capability using an electronic interface to a digital electronic display device 12. System 300 is an example embodiment including a wireless interface between a remote control device 13 and a button activator 14, as described above with respect to FIG. 16A. In addition, system 300 is an example embodiment including a wired interface between the button activator 14 and the electronic display device 12, as described above with respect to FIG. 17B. In other embodiments, other types of interfaces between remote control device 13 and button activator 14, and/or between button activator 14 and electronic display device 12, can be used as described above. System 300 includes a remote control 302, an interface assembly 304, and an electronic display device 306.

Remote control 302 or "remote FOB" is used as the remote control device 13 to send commands to the electronic display device 306. Remote control 302 can be any portable electronic device capable of transmitting one or more signals. In the described embodiment, the remote control 302 transmits signals wirelessly. For example, the signals can be transmitted as RF signals from an RF transmitter in the remote control 302. In one embodiment, the remote control 302 can include two buttons, where a first button causes a first page turn signal to be transmitted and intended to be interpreted as a "Page Forward" command, and a second button causes a second page turn signal to be transmitted and interpreted as a "Page Back" command. Another embodiment can provide only a "Page Forward" turn signal. In some embodiments, additional buttons and signals can be provided for additional page commands for the electronic display device 306, such as to display the first page at the start of a displayed document, to display the last page of a document, to display a page at a next chapter or user-defined bookmark, to access a particular page or document or page function of an application or the display device, etc. Remote control 302 can be implemented as a variety of devices, as described above with respect to FIG. 10. In other embodiments, the remote control 302 can transmit signals over a hardwired interface to the interface assembly 304, as described above with respect to FIG. 16C.

An interface assembly 304 is a device used to interface the remote control 302 with the electronic display device 306, and can be a "button activator" as described in embodiments above. In this described embodiment, assembly 304 includes a receiver block 310 and an I/O block 312. Other embodiments can provide the receiver block 310 and I/O block 312 as integrated in a single block, or divided into additional components as desired.

Receiver block 310 includes an RF receiver capable of receiving RF signals from the remote control 302. Circuitry is also included to generate signals based on the received RF button control signals, and these generated signals can be provided to the I/O block 312 to indicate that button control signals from the remote control 302 have been detected. In some embodiments, the receiver block 310 is connected to one or more batteries or other power source.

I/O block 312 is used to receive the signals that were generated by the receiver block 310 in response to receiving transmitted button control signals from the remote control 302. I/O block 312 interprets the signals provided by the receiver block 310 and generates device control signals appropriate for the electronic display device 306, sending these device control signals to the device 306 via a wired interface 314. In other embodiments (as indicated above for FIG. 17C), a wireless interface can be used between I/O block 312 and the device 306. The I/O block 312 can be implemented as a electronic circuit board receiving the signals from the receiver block 310 on wire connections or other interface, and generating appropriate device control signals for the device 306. Some embodiments of the I/O block 312 are described in greater detail below with respect to FIG. 21.

Other embodiments can provide a receiver block 310 integrated with the I/O block 312 that, based on receiving button control signal(s) from the remote control 302, directly generates one or more device control signals usable by the display device 306 as page commands to control the application's displayed image.

The wired connection 314 to the electronic display device 306 can in some embodiments terminate in a connector 317 that plugs into or otherwise mates with a connector 318 on the display device 306. In some embodiments, the connector 317 can be provided on a housing of the interface assembly 304, or provided at locations remote from the interface assembly 304. For example, in a music-reading embodiment, the interface assembly 304 can be located within a music stand, and the wired connection 314 can be a wire routed to a top portion of the stand, where the connector 317 is located. The connector 318 of the display device 306 can then be easily mated with the connector 317 as the device 306 is placed on the top of the music stand, ready to be used to display sheet music.

Electronic display device 306 can be any display device capable of displaying images such as documents (or other data collections having pages) on a display screen of the device. Device 306 can include electronic circuitry as described above with respect to FIG. 11 and other figures. The embodiment in this example is described using an iPad as the electronic display device 306. In other embodiments, other iOS (iPhone Operating System) display devices can be used, or other types of electronic display devices, as described above with reference to FIGS. 1-19. Device 306 can display images including pages of a document accessible by the device 306, where the device control signals received from the interface assembly 304 are operative to control an application running on the display device 306 to control the display of an image, such as displaying a different page of a document displayed on the device.

The electronic display device 306 can include a connector 318 to which the interface assembly 304 is connected by a wire, and through which the I/O block 312 sends signals to the device 306. For example, connector 318 can be a docking port connector of the device 306 which can connect to various hardware accessories. In some embodiments, the connector 317 can support the device 306 as a physical stand via the connector 318.

Application code 316 can be provided to run on the electronic display device 306. In the present example, application code 316 is an application that receives the control signals provided by the I/O block 312 and commands display functions of the device 306. In the present example, the application code 316 determines when a control signal is received and displays a different page of a document on the display screen of the electronic display device 306. For example, if a Page Forward command is received, the next page of the document is displayed in place of a current page. If a Page Back command is received, a previous page of the document is displayed. Other commands can also be implemented, as described herein. In other embodiments, the application code 316 can be only an interface portion of the code which communicates with a separate application viewer program that displays images such as a document.

Figure 21:
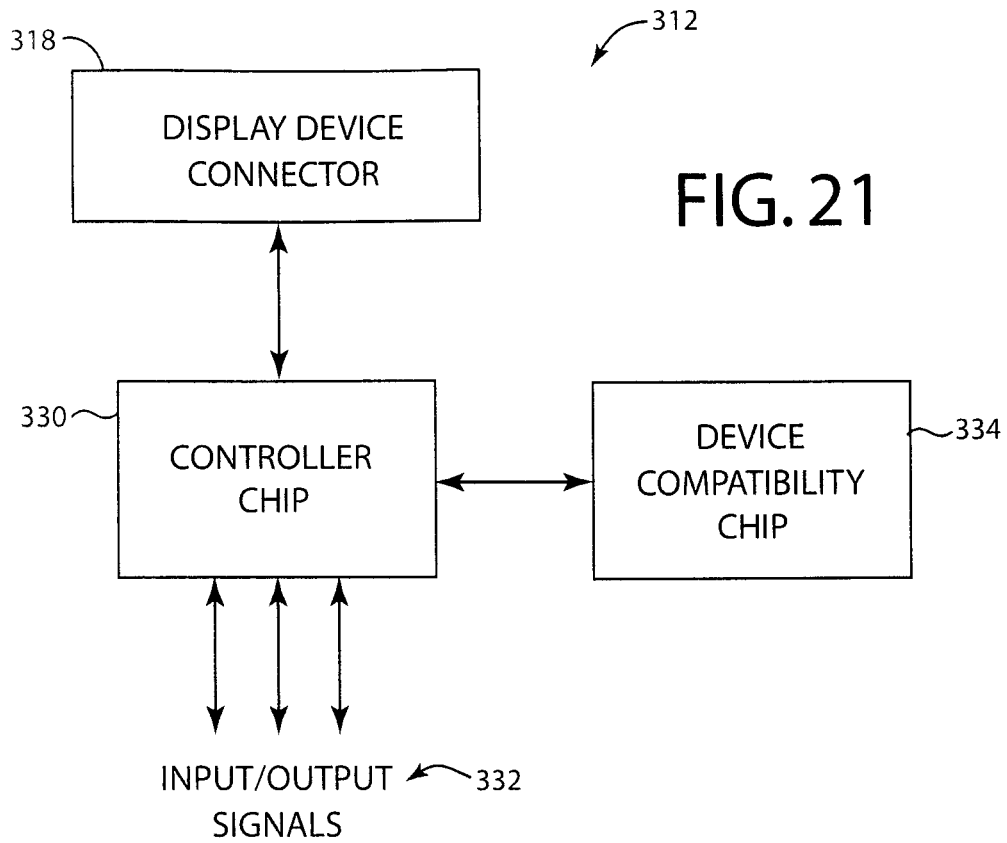
FIG. 21 is a block diagram illustrating one embodiment of an I/O block of the interface assembly in the system shown in FIG. 20.

FIG. 21 is a block diagram illustrating one embodiment of the I/O block 312 of the interface assembly 304 in the system 300 as shown in FIG. 20. The I/O block 312 is used to capture one or more signals from the receiver block 310 and interface with the application code 316 running on the electronic display device 306. I/O block 312 can be implemented on a printed circuit board. In some embodiments, there may be a thickness requirement to a printed circuit board which interfaces with the connector 318 of the display device; e.g., Apple Inc. has a thickness requirement of 31 mils in direct connect boards that connect to the 30-pin connector 318 of an iPad.

The I/O block 312 can include a controller chip 330 which is used to control the functions of the I/O block 312. Controller chip 330 receives input signals 332 and sends output signals 332 to and from components such as the receiver block 310 and other components of the I/O block 312, such as memory, buffers, or other standard components (not shown). The I/O block 312 thus effectively is used in the decoding of the received button control signals to provide device control signals. For example, a number of digital I/O lines (signal paths) can be provided to capture one or more signals provided by the receiver block 310 from the remote control 302. In one embodiment, one or more of the digital I/O lines 332 each provides an interrupt signal to firmware executing on the controller chip 330 to indicate that a page command signal has been received from the remote control 302. In other embodiments, other interrupts based on a change of signal can be used for other signals received from the remote control 302.

A device compatibility chip 334 can be provided in some embodiments to provide the necessary signals to the electronic display device 306 to cause the I/O block 312 to appear as an authorized device to the device 306 and permit the I/O block 312 to interface with the device 316. For example, in an embodiment using an iPad as device 306, the device compatibility chip 334 can be an "Apple chip" provided by Apple, Inc. which includes specialized code and provides authorized signals to identify itself to the operating system of the iPad to authenticate the I/O block 312 for use with the iPad 306.

The controller chip 330 provides control signals to the electronic display device 306 by sending signals via wire to the device connector 318 attached to the device 306. For example, in the example using the iPad as device 306, the connector 318 is a standard 30-pin connector that is the primary interface of the iPad to hardware accessory devices. The communications between the controller chip 330 and the iPad 306 can be, for example, via serial USART (universal serial asynchronous receiver/transmitter) operating at, for example, about 19.2 kbps or other suitable data rate.

In one example, the controller chip 330 can be a Microchip Inc. PIC16 embedded processor running at about 4 MHz clock speed set via internal clock. If no crystal oscillator is used, the tolerance of the clock is relatively inaccurate but acceptable for the functions of particular embodiments. In some embodiments, the controller chip 330 executes C code with about 50% of the program memory utilized, and approximately 80% of the code handling the establishing of secure communications to and from the OS on the iPad 306.

Figure 22:
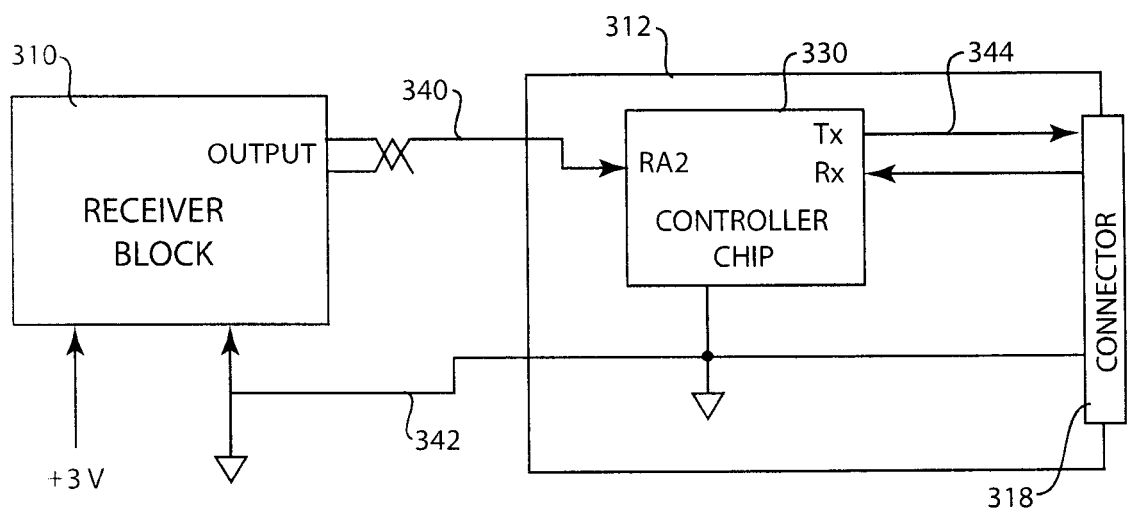
FIG. 22 is a block diagram illustrating signals provided between the receiver block and the I/O block of the interface assembly of FIG. 20.

FIG. 22 is a block diagram illustrating signals provided between the receiver block 310 and the I/O block 312 in an example embodiment. In this described embodiment, the receiver block 310 can be a multi-use component usable in different embodiments such as mechanical embodiments described in Figures above in addition to electronic control embodiments of the system 300. For example, in response to the receiver block 310 receiving the appropriate RF signals as transmitted by the remote control 302, the receiver block 310 can generate one or more pulse train signals (or PWM signals as described above) which can be used for multiple different applications. In one application of a mechanical embodiment, positive pulse train signals (e.g., 0 to about 3 volts) can be used to control motors driving mechanical or other physical portions of the button activator 14 to physically press buttons on the electronic display device 12, as described above with respect to FIGS. 6 and 17A, or to drive motors to input gestures on a touchscreen of the display device 306, as described above with respect to FIGS. 18 and 19. In the currently-described embodiment, the same receiver circuitry can be used, where such pulse train signals can be used to control the electronic display device 306 via electronic signals and, e.g., not a mechanical interface. In such an embodiment, the pulse train signals 340 (or other signals in other embodiments) are provided by the receiver block 310 to the I/O block 312. In one such embodiment, the signal 340 can be an independent 2-wire signal provided on a 2-wire line.

The output signal from the receiver block 310 can be captured by the I/O block 312, e.g., by an interrupt on change (IoC) signal line. For example, an "RA2" input of the controller chip 330 can be connected to the signal line providing signal 340, where chip 330 is a PIC 16F690 controller chip. This chip provides eight interrupt lines that can cause an internal interrupt based on a change to that line. Some of the eight lines can already be in use, e.g., as transmit (Tx) and receive (Rx) lines and SPI interface lines.

In the described embodiment, a ground signal 342 from a power supply (not shown) is used as a reference, connected to a ground plane of the board of the I/O block 312. The line 340 and ground 342 provide a 2-wire path such that the I/O block 312 can see and reference the output signal from the receiver block 310. In embodiments in which the output signal is a pulse train, the pulse train is seen by the controller chip 330 on the RA2 IoC line as a series of several interrupts. The controller chip 330 in some embodiments is programmed to only activate on positive-going changes (0 v to 3 v) such that half the signal changes are captured.

In a pulse train signal embodiment, the change in signal level can cause multiple interrupts to be generated on the board, although only one interrupt is needed for a pulse train generated by the receiver block 310. Thus, in one implementation, a software counter can be used to count each positive signal change (i.e. read as an interrupt) of the pulse train signal. After a predetermined counter number is reached, the counter is reset and a flag is set. In the main program loop of the controller, if the flag is determined to have been set, a command is built as a discrete digital device control signal and is sent to the display device 306 over the transmit (Tx) serial line(s) 344 and to the connector 318 of the display device 306. This command is interpreted as a page command for the application code 316. For example, in one embodiment a count of 200 positive-going changes can be used to trigger the signal to the display device 306, although this is dependent on the signals used in a particular embodiment. Thus the I/O block 312 can convert a pulse train signal from the receiver block 310 to a discrete logic-level digital signal for use with the application code 316 of the electronic display device 306.

Figure 1B:
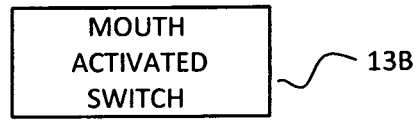
FIG. 1B is a representation of a mouth activated switch 13B which, by way of non-limiting example, can serve as a remote control device 13 of FIG. 1.

In some embodiments, the I/O block 312 can also receive inputs from remote control devices 13 implemented as physical switches connected to the I/O block 312 via wired or wireless connections. Such physical switches can provide enhanced input or interface for the user to provide page commands to the display device 306. For example, foot pedal 13A, as described above, including a physical switch can be connected to the I/O block 312 which can be used to send a page forward signal or command to the display device. Such a foot pedal can be useful to users who have their hands otherwise occupied or disabled, such as musicians playing an instrument and wanting to turn a page of sheet music displayed on the device 306. Another type of physical switch is one or more larger buttons, dials, levers, or other types of controls, which may be of use to people having difficulty pressing small buttons on the remote control unit. Another type of physical switch capable of serving as remote control device 13 is a sip or blow switch ("mouth activated switch"), which allows the user to send one or more signals based on manipulation, by way of non-limiting example, of a mouth activated switch 13B of FIG. 1B, such that the remote control device 13 includes a switch activated by the user's mouth, which can be useful for disabled persons, for example. Connection interfaces such as input/output jacks or connectors can be provided on the housing of the interface assembly 304 or other housing enclosing the I/O block 312 to connect to additional switches. For example, common headphone jacks can be provided on a housing of the I/O block 312 or a separate housing.

Additional I/O lines can be provided on the board of the I/O block 312 in other embodiments. For example, a different PIC controller such as the PIC16LF1936 can be used to handle additional IoC lines to handle additional switches. The firmware of the controller chip 330 can also be changed to accommodate different types of signals. For example, instead of counting pulses in a pulse train signal from the receiver block 310 and sending the command after a predetermined count of interrupts is reached as described above, the controller chip 330 can send the command signal at each received interrupt, since each interrupt can be associated with a single activation (e.g. button press or other switch activation). Additional loops can be added to monitor additional switches.

Figure 23:
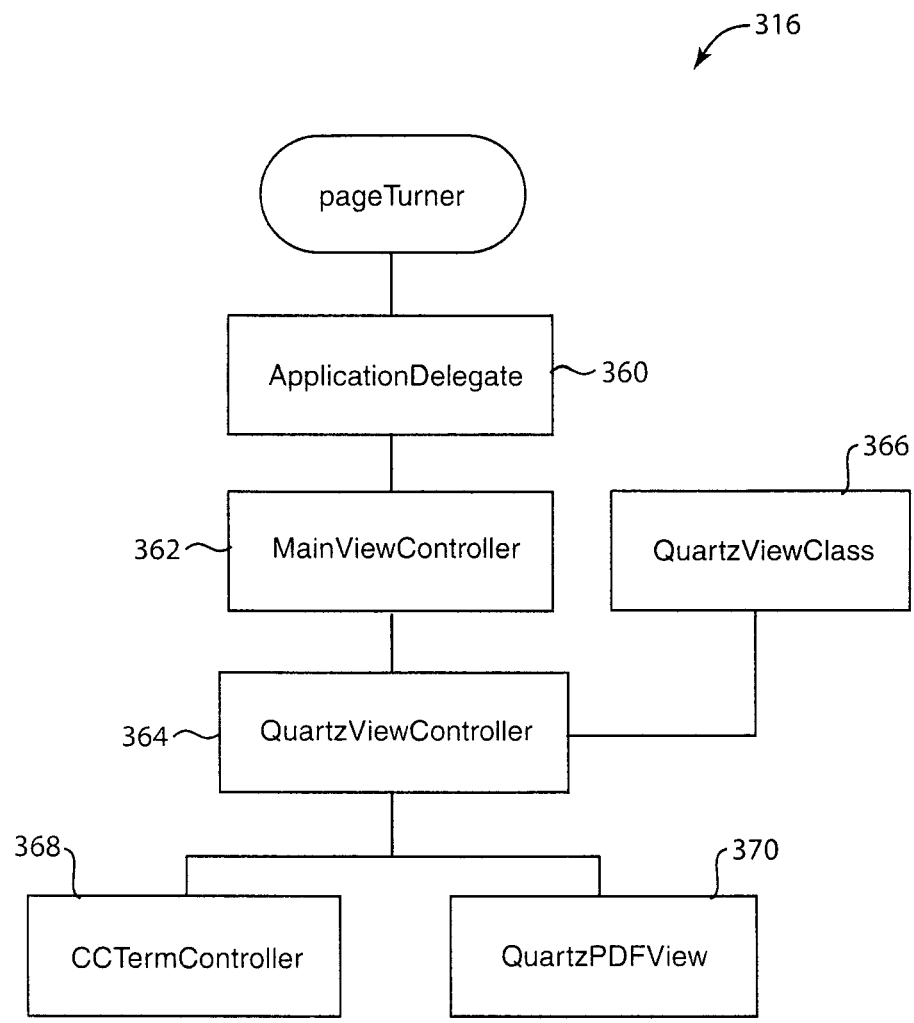
FIG. 23 is a block diagram illustrating an example of a hierarchy of application code running on the electronic display device.

FIG. 23 is a block diagram illustrating an example of a hierarchy of software for the remote page command application code 316 running on the electronic display device 306. In the described example, the application provides page viewing ability for a displayed image runs on the device 306 under an operating system of the device, which is the iOS of an iPad or iPhone device 306 in this example. The application displays a document on the display screen of the electronic display device 306 and receives commands (such as particular signals or values) from the I/O block 312 to cause a next page (or other page as per the command) to be displayed by the application on the device 306 in accordance with the commands. In one example, a PDF (Portable Document Format from Adobe Systems, Inc.) document can be displayed by the application on device 306.

In one embodiment, the remote page command application code 316 includes two main functions: a viewing program that displays documents, and an interface object or function (or "notification object") used to received the device control signals from the I/O block and command the viewing program. In one example, the viewing program is a modified version of a program called QuartzView available from Apple, Inc. for the iPad or iPhone. The QuartzView program provides developers working knowledge of using Quartz, a 2D library of routines that support basic drawing in Cocoa (an application programming interface (API) for Apple computer products) and for the iPhone/iPad. The notification object is called "CCTermController" in FIG. 23, and is an object that provides access to external accessories, such as the I/O block 312, through a standard interface such as the Apple External Accessory Framework. A framework is similar to a library, providing a standard set of calls to functions that are not included in the base operating system. These frameworks are included through function headers (e.g., #import statements) and linking in the appropriate framework during the build of the application or project.

As shown in the example of FIG. 23, the page command application code can include a hierarchy of objects used in an object-oriented framework on the electronic display device 306. For example, the ApplicationDelegate object 360 represents the most common point across all the objects and acts as a "delegate" for the application itself, performing initialization and setting up the first view or image displayed by the device 306. The MainViewController object 362 is the first view controller that a user sees displayed by the device 306, and provides a selection of programs or functions that the user can select to be executed. One such program is the viewer program used to display a document or other set of images having multiple pages. For example, a PDF viewer program can be one of the items displayed by the MainViewController 362. The MainViewController 362 can also be configured display a description of the document that is presented as an option to select. The QuartzViewController object 364 is a subclass of the more generic QuartzView class object 366. The QuartzViewController object 364 uses a QuartzPDFView object 370 to manipulate PDF documents.

The CCTermController object 368 is a notification object that interacts with the connection to the I/O block 312 external to the display device 306 and connected via the connector 318. For page turning functionality, this code provides a "page" notification that is broadcast each time data is received from the I/O board 312 via the connector 318. Any other objects subscribed to the notification object and listening for the notifications will detect them upon the broadcast, and perform actions in response to receiving the notifications, such as changing the display on the device 306 in accordance with the notification.

The application code 316 can also be changed in some embodiments to accept additional and/or multiple types of input signals from the I/O block 312 such as from additional switches. Thus the application code can be provided with a protocol to distinguish what type of signal it has received, such that the I/O block 312 sends a different signal or value for different page commands such as Page Forward, Page Back, etc. The CCTermController object of the application code can create and broadcast different notifications, each type of notification associated with a different type of signal /page command. The object that actually performs the page turning function and display of the application can subscribe to each of the different types of notifications and act according to any notification received.

Some examples of interfacing with an accessory for an iPhone OS for use with an iPhone or iPad are described in *Building iPhone OS Accessories*, by Ken Maskrey, 2010, from Apress, which is incorporated herein by reference in its entirety.

When operating the system 300, an example of a procedure of operation is now described. This procedure is only one example of many possible operation procedures. The receiver block 310 is powered on by a pushbutton or other control. The electronic display device 306 can then be powered, and displays a menu screen including an icon which can be selected to run an associated viewer program, such as the remote page command application code 316 described above. For example, the user can tap the screen to select this icon.

In one example, the device 306 can display a "tableview" provided by the MainViewController object 362 after the application icon has been selected by the user on a previous first menu screen. The tableview can be a list of available documents, and in this example includes a selection for the page command application. If the user then selects (e.g., taps) the single row in the tableview for the application, the first page of an associated document is displayed. In other embodiments, a list of different documents can be displayed in the tableview, any of which the user can select for display of the appropriate first page.

The user can command the next or previous pages of the document to be displayed using the normal interface of the device 306. For example, using an iPad, the user can perform a "swipe" finger gesture to the right on the display screen to display the next page, or to the left to display the previous page.

The interface assembly 304 can be connected to the device 306 at the connector 318 of the device 306, such as by plugging in a mating connector on the assembly 304 or I/O block 312. The user can now select a page forward button on the remote control 302, which causes the next page of the document to be displayed by the device 306. In some embodiments, the user can select a page back button or other buttons or controls to command the device 306 to perform other functions related to the document.

In embodiments such as the iPad or iPhone, there may be restrictions for the application code in some circumstances. For example, a "provisioning profile" may need to be created on a developer site for a particular set of devices for a particular application. Users who wish to use the program can load the provisioning profile using a configuration utility and load the program to their device. Such procedures are well known for particular devices such as the iPad and iPhone.

Figure 24:
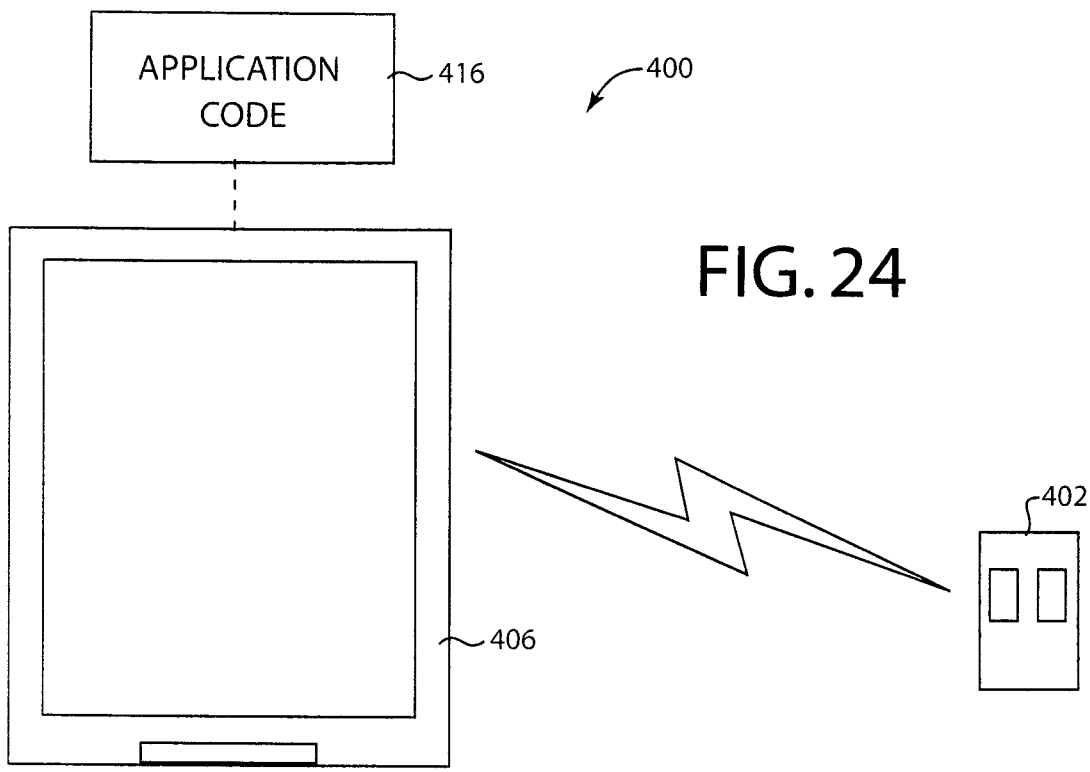
FIG. 24 is a block diagram illustrating another embodiment of a remote control system for an electronic display device using a wireless interface.

FIG. 24 is a block diagram illustrating another embodiment 400 of a remote control system for an electronic display device. In this embodiment, a wireless connection is used to directly command the display device 306 from the remote control. A built-in wireless communication component of the display device 306 is used, such that there is no separate receiver block, I/O block, or physical wired connection from the I/O block to a connector of the display device as in the embodiment described above with reference to FIG. 20. Since no physical or electrical connection is made with the display device 306, the device 306 has less chance of being damaged by mishandling or static discharge between devices as compared to the embodiment of FIG. 20. The system 400 includes a remote control 402 and an electronic display device 406.

Remote control 402 is used to transmit commands selected by a user to the electronic display device 306. The remote control 402 includes all necessary electronics to transmit wireless signals, such as RF signals. Other embodiments can use other types of signals and/or connections, such as IR, wireless network, etc. as described with respect to FIGS. 16A-16E. The remote control 402 can include one or more buttons or other switches or controls to be manipulated by a user, similarly to the remote control 302 of FIG. 20, for providing transmitted commands. For example, buttons for Page Forward, Page Back, and/or navigating to other portions of a document can be provided on the remote control 402.

Electronic display device 406 can be similar to the device 306 of FIG. 20, and is described in this example as an iPad. Device 406 receives wirelessly-transmitted button control signals from the remote control 402 to control an application running on the display device to change a displayed image of the device 406, such as changing the page of a document displayed by the application. For example, the electronic display device 406 can in some embodiments be the display device 12E of FIG. 17E described above, which includes an integrated button activator 14E. Such an integrated button activator can be, for example, code integrated in an application running on the device 406. In other embodiments, the remote control device 402 can be considered to have the integrated button activator, as described above with reference to FIG. 16E.

In the described embodiment, the remote control 402 communicates with the device 406 using a standard wireless communication protocol, such as Bluetooth®. Other types of protocols or standards can be used in other embodiments.

The Bluetooth standard provides a short-range, wireless communications standard for exchanging data between devices. Bluetooth is defined as a layer protocol architecture consisting of core protocols, cable replacement protocols, telephony control protocols, and adopted protocols. Some of these are basic, more common functional protocols of Bluetooth found in commonly available devices; for example, a common Bluetooth application is wireless headsets used with cellular phones for hands-free exchange. Two common protocols are the Telephone Control Protocol and Telephony control protocol-binary (TCP-BIN). TCS-BIN is a bit-oriented protocol that defines call control signaling for the establishment of voice and data calls between Bluetooth devices such as a headset and a cell phone. Another commonly-found protocol in portable music players (e.g., MP3 players) is the Audio/Visual Data Transport Protocol (AVDTP) used to stream music to stereo headsets over an L2CAP (Logical Link Control and Adaptation Protocol) channel. An L2CAP channel is used to multiplex multiple logical connections between two device using different higher-level protocols.

In the example embodiment of system 400, a different Bluetooth protocol can be used, known as RFCOMM (radio frequency communications). RFCOMM is a protocol used to replace a cable connection, and creates a virtual serial data stream. RFCOMM provides for binary data transport and emulates RS-232 (serial) control signals over the Bluetooth baseband layer, and provides a simple, reliable data stream to the user, similar to TCP. For example, it is used directly by many telephony related profiles as a carrier for modem AT commands, as well as being a transport layer for OBEX (Object Exchange) over Bluetooth. Many Bluetooth applications use RFCOMM because of its widespread support and publicly available API on most operating systems. Additionally, applications that used a serial port to communicate can be quickly ported to use RFCOMM.

Figure 25A:
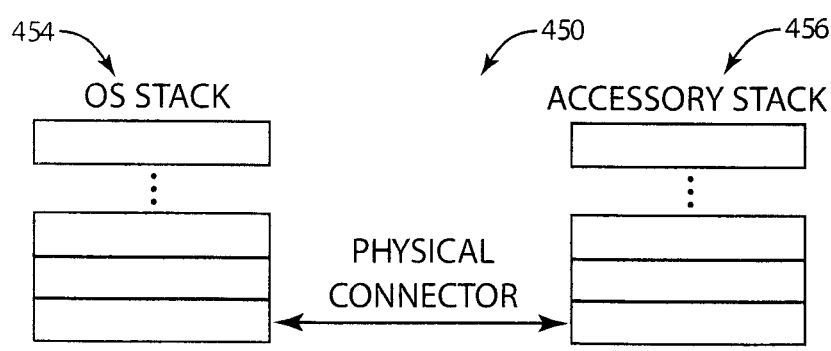
FIGS. 25A and 25B are diagrams illustrating software stacks for the systems of FIG. 20 and FIG. 24.
Figure 25B:
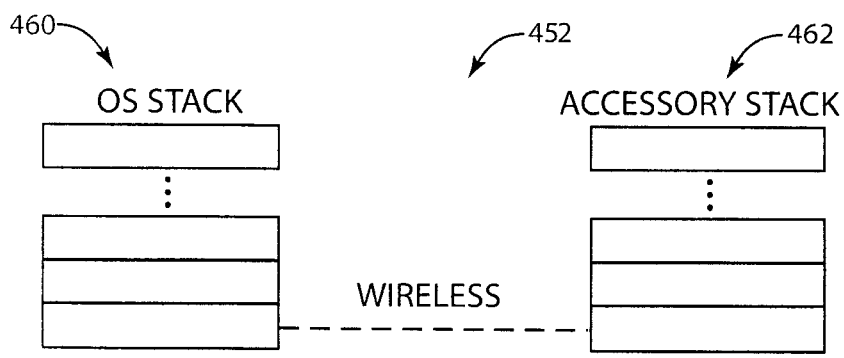

The electronic display device 406 can include a software stack similar to that of device 306 described above for system 300. FIGS. 25A and 25B are diagrams illustrating the software stacks for two systems, where FIG. 25A illustrates a software stack system 450 for the system 300 of FIG. 20 using a wired connection and physical connectors, and FIG. 25B illustrates a software stack system 452 for the system 400 of FIG. 24 using a wireless connection. In FIG. 25A, an OS stack 454 includes software components and application code, including everything from the top level applications to the lower-level drivers and software at the bottom of the stack that allow communication over the physical pins of connector 318. An accessory stack 456 resides on the interface assembly 304, such as in the I/O block 312, and includes the higher-level code, interrupt routines, and lower-level software components for communicating over the physical connector 318, such as protocol code, USART transmission control routines, counters, etc.

In FIG. 25B, a similar OS stack 460 includes software components and application code. The bottom of the stack 460 includes components for handling Bluetooth communication, which is built into display devices such as the iPad and iPhone. The Bluetooth connection communicates with an accessory stack 462 similarly to the embodiment in FIG. 25A, except that in this embodiment the communication is wireless Bluetooth and the accessory stack 462 resides on the remote control 402. The lowest level components of the accessory stack 462 on the remote control 402 transmit and receive signals over the Bluetooth protocol. Thus the stacks of FIG. 25B are essentially the same as the stacks for FIG. 25A except for the lowest level components using wireless communication instead of wired communication.

Referring back to FIG. 24, in some embodiments, the wireless system 400 can use application code 416 running on the electronic display device 406 that is the same as the application code 316 running on system 300 of FIG. 20. In such an embodiment, the application code 416 receives control signals from the remote control 402, such as values indicating the particular command sent. The application code 416 includes viewer application code to display the next page, previous page, or perform a different page function as indicated by the received command.

In another embodiment, existing applications can be modified by developers to be compatible with the remote control system 400. For example, existing reader or viewer applications such as iBooks from Apple, Inc., Kindle (from Amazon.com) for the iPad, and Stanza from Lexcycle, Inc., can display a next page, previous page, or perform some other function commanded by the remote control 402. In one such embodiment, an application developer can license the functionality of the page-turning system 400 to use with his or her application.

Adding page-turning capability to an existing application enhances the functionality of the application and expands the user base. For example, the user experience is enhanced by providing people with limited mobility the ability to use the application. This applies to people with inherent limited mobility as well as situational limited mobility, e.g., people performing a task in a situation where their hands are not free to initiate gestures or otherwise control the device 406 to turn pages or perform other functions. For example, musicians may have their hands occupied playing an instrument and yet need to turn pages of a musical score.

In one example of a developer adding functionality to interface with the page-turner remote control 402, particular steps can be performed. The steps can include the application owner or developer contacting a company controlling the page turning system 400 to obtain a license. The company can "whitelist" the developer in a product plan for the product on a developer site, e.g. the Apple Made For iPod/Works With iPhone developer site. This allows a bundle seed identifier (a unique code) in the accessory hardware to be available to the application developer. The company can then provide the developer a set of remote page command code, such as the accessory controller object (notification object), to be added to the developer's software. In the embodiment of FIG. 23, this can be the CCTermController object. The company can also provide some guidance as to how the code is to be integrated into the developer's application. The developer then can add the code to his or her project and use the bundle seed identifier to re-build the application. At this point, the developer's application is compatible with and work with the remote control 402 to provide the page turning system 400.

The application developer also can modify his or her code so that signals from the remote control 402 cause displayed pages to turn. Generally, in the object where page numbering and/or turning is handled, the developer can add code to subscribe to the notifications provided by the notification object. The remote page command remote control 402 provides different page-turn notifications including forward one page, back one page, forward one chapter, back one chapter, forward to end of document, back to beginning of document, etc. The specific set of commands/notifications can be configurable by the developer or user. For example, a button, sequence of buttons, or type or configuration of button press (one press, two presses in succession, time interval between presses, etc.) can be configured by the user to be interpreted as different types of page commands by the application code 416.

Figure 26:
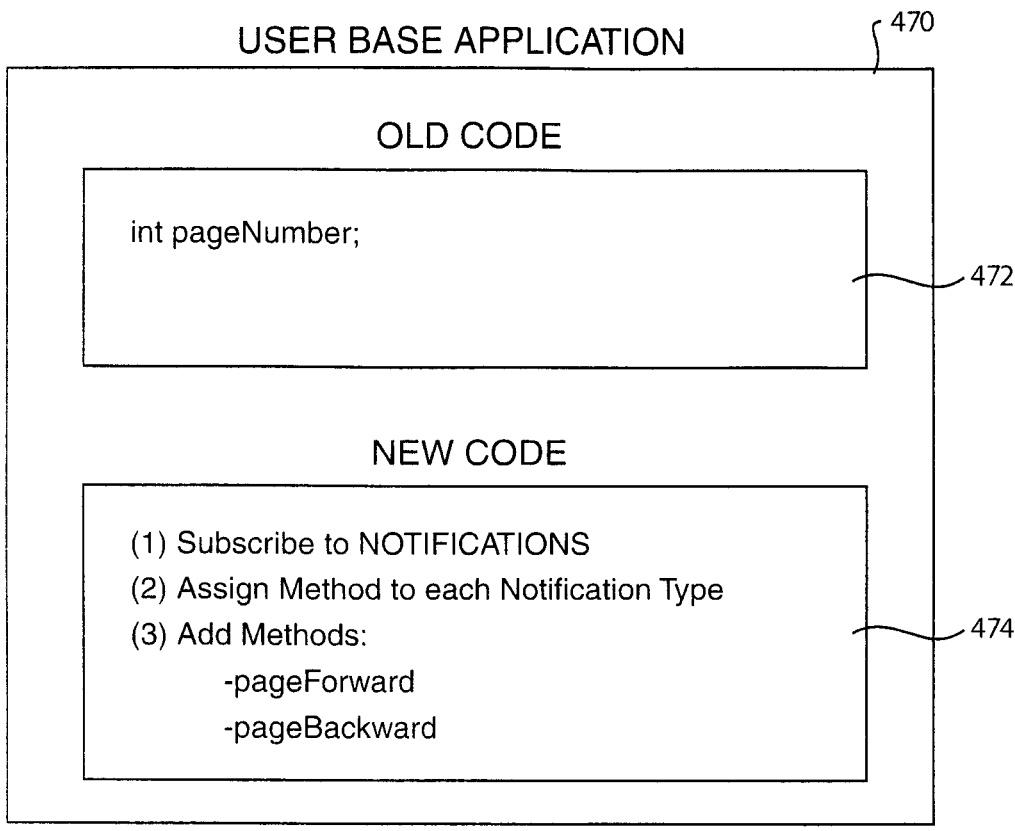
FIG. 26 is a diagrammatic illustration of an example of providing new code for an application running on the electronic display device to add compatibility with the page turning system of FIG. 24.

FIG. 26 is a diagrammatic illustration of an example of providing new code for an existing application which can run on the electronic display device 406 to add page command functionality and compatibility with the remote control system 400. The existing base application 470 includes baseline code including old code 472, where the old code includes a variable that contains the page number of a document being viewed. The base application already implements a mechanism for turning pages, which in the example of the iPad or iPhone is typically some type of gesture recognizer. For example, the existing code would read gestures such as left swipe or right swipe to page forward or page backward, respectively.

The existing gesture recognizers (or other page turning mechanism) include assigned methods to call when the internal recognizer detects or recognizes a particular gesture. Those methods are functions that page the document forward, backward, etc. Typically, they perform two actions: change a page number variable (or equivalent), and refresh the display to a new page through a method call to a function such as "setNeedsDisplay" (or other display function).

New code 474 can be put into the base application and, in the described example, can provide compatibility with the remote control system 400. Thus the code 474 can be provided as part of a "button activator" of the remote control system that is integrated in the device 406 and enables control over page functions of the device. For example, for each distinct signal (type of command) that is desired to be recognized from the remote control 402, a line of code can be added to the application, to the view controller object in which the page display is performed. In one example, the line of code can be as follows:

[[NSNotificationCenter defaultCenter]
addObserver: self
selector:@selector(pageForwardOneFromRemote):)
name:@ "pageForwardOne" object:nil];

This code (addObserver: self) adds itself as an observer of (subscriber to) the notification. Using the selector parameter, the method pageForwardOneFromRemote is added as the method that activates or "fires" when the notification is seen. The name of the notification that is looked for is specified as "pageForwardOne," and "nil" is passed to the object parameter. The "nil" indicates that no data is expected to accompany the notification. This is all "called on" or performed under the default notification center, of which there is only one in the application and is shared among all objects.

Alternatively, notifications can be sent accompanied with data, such as parameters further defining the page command. For example, the parameters can be the number of pages to move in any direction, the amount (in pixels, scaling factor, or other measure) of pan or zoom to be applied to the image displayed by the display device 406, or any other specifiable parameters.

A notification command such as shown in the code example above is defined for each type of notification that is to be processed by the application. These types of notifications can be for received page commands including pageForward and pageBackward as shown in the new code 474 of FIG. 26. Additional types can also be used, such as other navigation commands for a document (go to start, go to end, go to next chapter or user-defined bookmark, etc.)

The code example above monitors and acts upon received notifications. The notifications are generated by code supplied by the remote control system owner/provider in an accessory control object (notification object). Notifications are sent based upon the commands sent by the transmitter unit of the remote control 402 and received by the wireless receiver of the device 406. Notifications can always be sent regardless of whether or not the application on the device 406 monitors and acts upon the notifications. The notifications generated by the accessory control object go to a notification center and are forwarded to any object "listening" for (subscribed to) them. If no object is listening for the notifications, then no notifications are forwarded, i.e., the notifications are "dropped" without consequence.

The following code is provided as an example of the generation of a notification:

[[NSNotification Center defaultCenter]
postNotificationName:@ "pageForwardOne" object: self];

It should be noted that the posting of notifications is simpler than monitoring and reacting to them. Here, again using the default notification center, the "pageForwardOne" type of notification is posted to the notification center (used for causing the next page of the displayed document to be displayed). The "object" parameter identifies the sender of the notification as this object. Listeners can not only listen for particular notifications, but also for all notifications from named senders. It should also be noted that the names of the notifications can be any name defined by the developer of the code in a particular embodiment.

Figure 27:
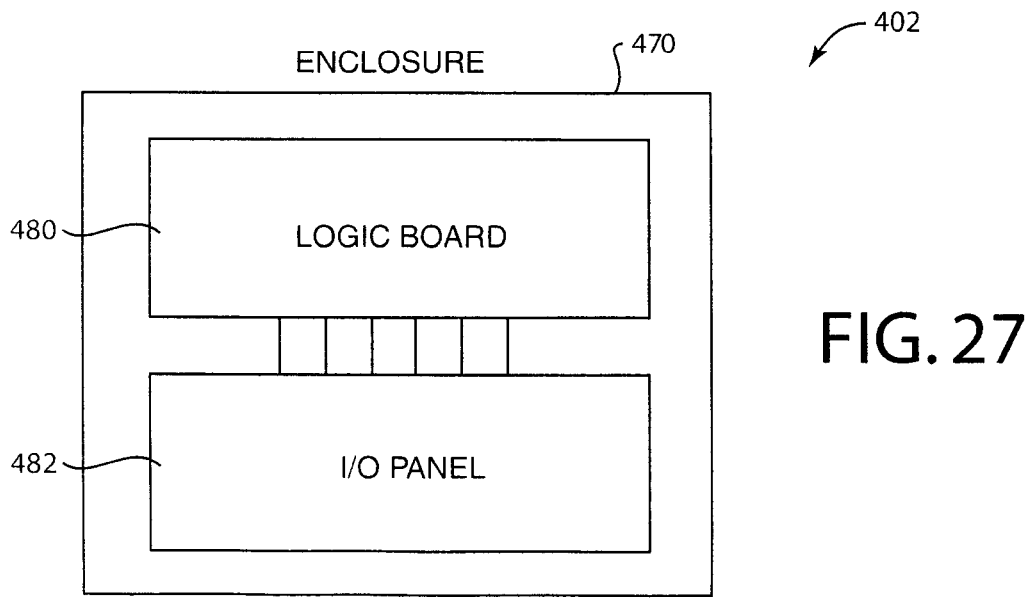
FIG. 27 is a block diagram illustrating an example of a hardware design for the remote control of the system of FIG. 24.

FIG. 27 is a block diagram illustrating an example of a hardware design for the remote control 402 of the system 400 of FIG. 24. In this embodiment, the remote control 402 includes an enclosure 480, an I/O panel 482, and a logic board 484.

The enclosure 480 can be any housing for enclosing and securing the electronic and other components of the remote control 402, such as I/O panel 482 and logic board 484. For example, the enclosure can be a box-like case having a form factor to house the desired components, including accuracy of fit and mounting holes. In one example, production units can be created using injection molding with ABS or ABS/PC (Acrylonitrile Butadiene Styrene/Polycarbonate) material. The I/O panel 482 provides one or more controls for the user to activate to provide an activation signal to the logic board 484 to cause the logic board 484 to send button control signals to the display device 406. Such controls can include buttons, dials, switches, etc. For example, I/O panel 482 can be in an area of the enclosure 480 that is configured for buttons and connectors such as 3.5 mm jacks, or any other desired controls and/or connectors. In one configuration, a pageForward button, a pageBackward button, a power switch, and a charging switch (for remote controls using a rechargeable battery design) can be provided, with holes in the enclosure provided for customized button sizes and positioning. Separate molds can be used for differently-sized remote control units.

The logic board 484 controls the operation of the remote control 402, including receiving activation signals from the I/O panel in response to the user activating one or more controls, and transmitting button control signals to the electronic display device in response to such activation signals. The board 484 accepts external control inputs from controls mounted in the enclosure 480 or from control such as remote switches connected to the I/O panel 482, e.g., switches connected via two-conductor wire routed to case-mounted 3.5 mm female jacks. Using such jacks (or other types of connectors) permits use of any type of remote switch to provide page commands in system 400, e.g., a foot pedal, a large button, a sip/blow switch usable by the mouth of a disabled person, etc.

Figure 28:
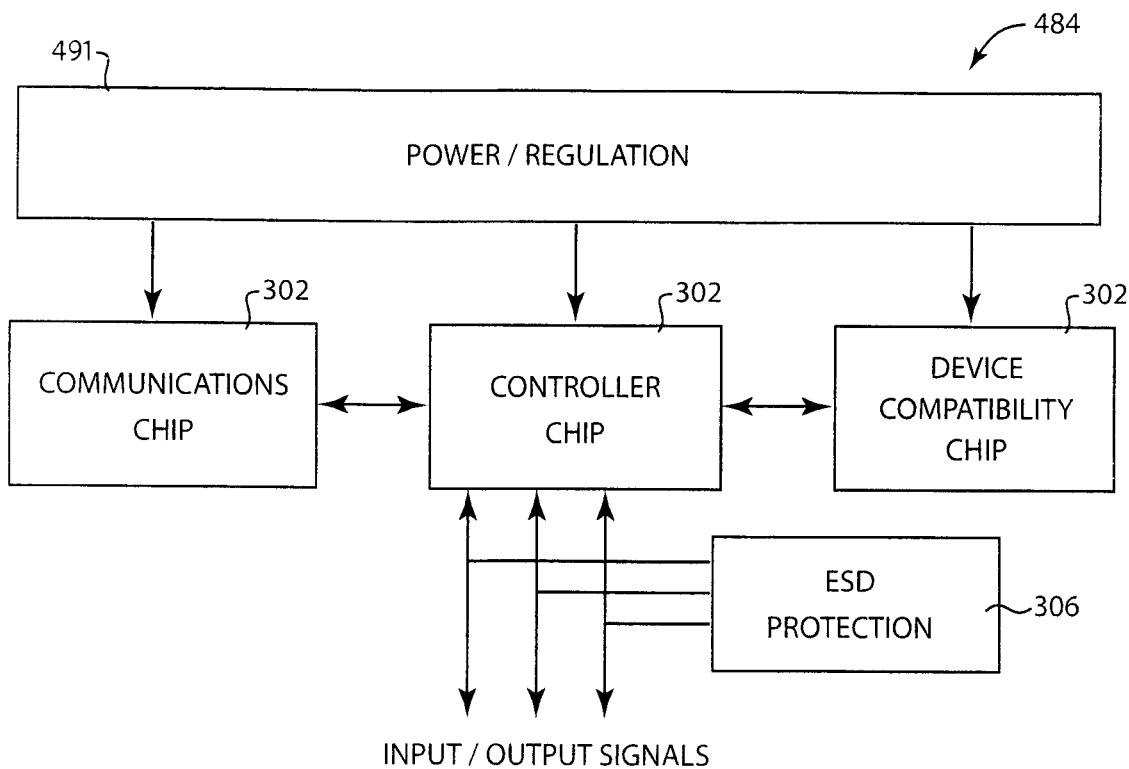
FIG. 28 is a block diagram illustrating one example of a logic board of the remote control of the system of FIG. 24.

FIG. 28 is a block diagram illustrating one example of the logic board 484 of the remote control 402. The logic board 484 can be a printed circuit board made of any suitable material, e.g., in one embodiment FR-4 (glass reinforced epoxy laminate) with 1 oz. copper traces or similar features can be used. In some examples, the logic board 484 can be made 3" by 3" or smaller, with four, six, or eight layers. Outer (top and bottom) layers can provide signal routing and inner layers provide Vdd (source voltage) and Vss (ground).

Figure 29:
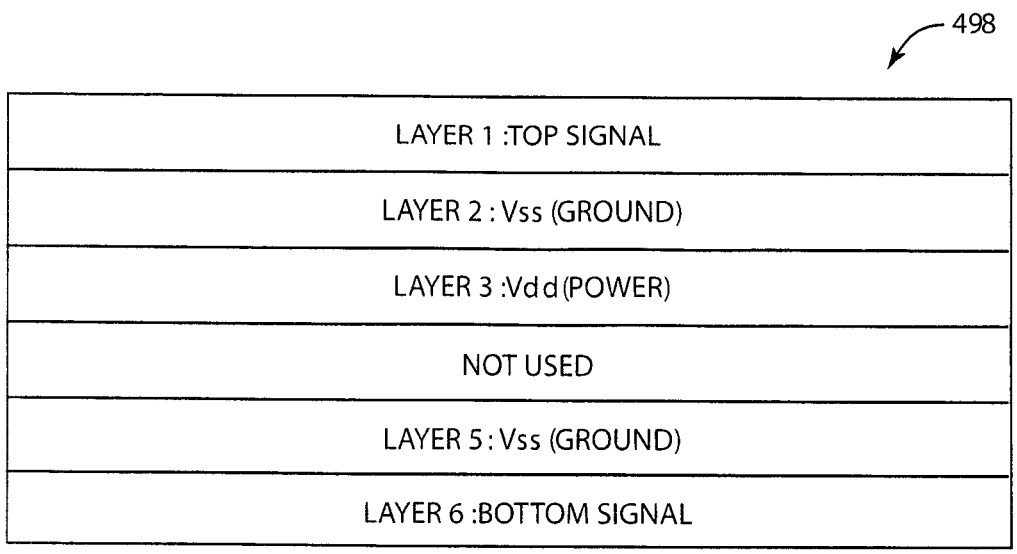
FIG. 29 shows an example of a six-layer printed circuit board that can be used in the logic board of FIG. 28.

FIG. 29 shows an example six-layer printed circuit board 498 that can be used in the logic board 484 of FIG. 28. In this example, signal layers are on the surfaces of the board, at layers 1 and 6, with the goal to not use any internal signal plane. Layers 2 and 5 can be used for the Vss signals (ground), and layer 3 can be used for Vdd (power).

Referring back to FIG. 28, a controller chip 486 can be provided on the logic board 484 to control the operation of the remote control 402. In one embodiment, the controller chip 486 can be a Microchip PIC 16 controller, such as the PIC 16F690 or PIC16LF1936, similarly as described above for the embodiment of FIGS. 21-22. Other processor chips can be used in other embodiments.

A communications chip 488 can be used to implement the wireless protocol and transmit appropriate signals compliant with the protocol. For example, in embodiments using Bluetooth as described herein, the communications chip 488 can be a Bluetooth communications chip that implements the Bluetooth protocol and provides additional features. For example, the CSR BlueCore5 chip includes a DSP, stereo CODED, flash, etc. The communications chip 488 communicates with the controller chip 486 as needed to provide appropriate wireless output signals from the remote control 402, where control software on the chip 488 interfaces with the communications chip 488.

The device compatibility chip 490 can be provided in some embodiments to provide the necessary signals to the electronic display device 406 to cause the remote control 402 to appear as an authorized device to the device 406 such that the commands from the remote control 402 are properly received by the device 406, similarly as described above for FIG. 21.

Power and regulation block 491 can provide power to the controller chip 486, communications chip 488, and device compatibility chip 490. For example, the block 491 can be a regulated power source providing sufficient power (e.g., nominally at 3.3 volts) to drive the remote control 402 for an expected time duration. The amount of power drawn by the remote control 402 is dependent on usage and number of I/O connections. For example, one or more batteries can supply the necessary power, and the remote control 402 can include power saving features as described above. The logic board 484 can also include ESD protection 492, such as protection diodes that protect all external input and output to and from the logic board 484, thus preventing damage to the board 484 and to the remote control 402.

The input and output signals 494 includes the signals used by the remote control, including output wireless button control signals to command the display device 406, and input activation signals from buttons and other controls connected to the remote control 402.

Although various examples have been described using specific terms and devices, such description is for illustrative purposes only. The words used are words of description rather than of limitation. In addition, it should be understood that aspects of various other examples may be interchanged either in whole or in part. It is therefore intended that the claims be interpreted in accordance with their true spirit and scope and without limitation or estoppel.

What is claimed is:

1. A remote control system comprising:
    a remote control device including at least one control operative to develop at least one button control signal in response to activation by a user; and
    an interface device including a logic circuit responsive to said at least one button control signal and operative to provide at least one device control signal via a wired connection to an electronic display device having a display and one or more buttons to control an image on the display, the at least one device control signal operative to control an application running on the electronic display device to determine which button of the electronic display device is activated to control the image that is displayed;
    wherein the interface device is connected to the electronic display device via a docking port connector of the electronic display device.

2. The remote control system as recited in claim 1 wherein the remote control device includes a wireless transmitter and the at least one button control signal is wireless, wherein the interface device includes a receiver responsive to said at least one wireless button control signal.

3. The remote control system as recited in claim 1 wherein the remote control device is connected to the interface device via a hardwired connection and wherein the at least one button control signal is a signal provided over the wired connection.

4. The remote control system as recited in claim 1 wherein the remote control device includes a foot pedal operative to develop the at least one button control signal.

5. The remote control system as recited in claim 1 wherein the remote control device includes a switch activated by a user's mouth, the switch operative to develop the at least one button control signal.

6. The remote control system as recited in claim 1 wherein the application displays an image on a display of the electronic display device and the at least one device control signal is operative to control the display of the image.

7. The remote control system as recited in claim 6 wherein the control of the display of the image includes displaying a different page of a document displayed by the application in response to the at least one button control signal.

8. The remote control system as recited in claim 1 wherein the application running on the electronic display device receives a notification from a notification object running on the electronic display device, the notification provided in response to the electronic interface device receiving the at least one device control signal from the interface device.

9. A remote control system comprising:
    at least one control operative to develop at least one activation signal in response to activation by a user; and
    an interface device including logic circuitry coupled to the at least one control and operative to receive the at least one activation signal, the logic circuitry including a wireless transmitter operative to transmit at least one device control signal wirelessly to an electronic display device having a display and one or more buttons to control an image on the display, the electronic display device including a wireless receiver operative to the at least one device control signal, wherein the at least one device control signal is operative to control an application running on the electronic display device to determine which button of the electronic display device is activated to control the image that is displayed to change a display of a document displayed by the application on the electronic display device.

10. The remote control system as recited in claim 9 wherein the change of the display of the document includes displaying a different page of a displayed document in response to the at least one activation signal.

11. The remote control system as recited in claim 9 wherein the control and logic circuitry are disposed in a single remote control enclosure.

12. The remote control system as recited in claim 9 wherein the at least one device control signal is recognizable by a wireless-capable component of the electronic display device.

13. The remote control system as recited in claim 9 wherein the wireless transmitter transmits the at least one device control signal according to a Bluetooth wireless protocol.

14. The remote control system as recited in claim 9 wherein the at least one control includes a foot pedal operative to develop the at least one activation signal.

15. The remote control system as recited in claim 9 wherein the at least one control includes a switch activated by a user's mouth, the switch operative to develop the at least one activation signal.

16. The remote control system as recited in claim 9 wherein the remote control system further comprises a button activator comprising code running on the electronic display device for commanding the application to change the display.

17. The remote control system as recited in claim 16 wherein the code running on the electronic display device comprises a notification object such that the application receives a notification from the notification object, the notification provided in response to the electronic interface device receiving the at least one device control signal from the logic circuitry.

18. A method for remotely controlling an electronic display device, the method comprising:
    providing a button control signal from a remote control device in response to a control on the remote control device being activated by a user;
    connecting an interface device including an interface circuit to an electronic display device via a docking port connector of the electronic display device, the electronic display device having a display and one or more buttons to control an image on the display; and receiving said button control signal at the interface device, decoding said button control signal using a digital processor of the interface circuit to derive a device control signal, and providing the device control signal to the electronic display device, the at least one device control signal operative to control an application running on the electronic display device to determine which button of the electronic display device is activated to control the image that is displayed.

19. The method as recited in claim 18 wherein the application displays an image on a display of the electronic display device and the at least one device control signal is operative to control the display of the image, wherein the control of the display of the image includes displaying a different page of a document displayed by the application in response to the at least one button control signal.

\* \* \* \* \*